United States Patent
Meulewaeter

(10) Patent No.: US 10,544,423 B2
(45) Date of Patent: Jan. 28, 2020

(54) RECOMBINANT PROMOTER WITH INCREASED FIBER-SPECIFIC EXPRESSION

(71) Applicant: BASF Agricultural Solutions Seed US LLC, Research Triangle Park, NC (US)

(72) Inventor: Frank Meulewaeter, Merelbeke (BE)

(73) Assignee: BASF Agricultural Solutions Seed US LLC, Research Triangle Park, NC (US)

( * ) Notice: Subject to any disclaimer, the term of this patent is extended or adjusted under 35 U.S.C. 154(b) by 76 days.

(21) Appl. No.: 15/518,777

(22) PCT Filed: Oct. 15, 2015

(86) PCT No.: PCT/EP2015/073931
§ 371 (c)(1),
(2) Date: Apr. 13, 2017

(87) PCT Pub. No.: WO2016/062615
PCT Pub. Date: Apr. 28, 2016

(65) Prior Publication Data
US 2017/0247712 A1    Aug. 31, 2017

(30) Foreign Application Priority Data
Oct. 21, 2014  (EP) .................... 14189642

(51) Int. Cl.
C12N 15/82    (2006.01)
A01H 5/08     (2018.01)
C12N 9/10     (2006.01)

(52) U.S. Cl.
CPC ........... C12N 15/8235 (2013.01); A01H 5/08 (2013.01); C12N 9/1051 (2013.01); C12Y 204/01016 (2013.01)

(58) Field of Classification Search
None
See application file for complete search history.

(56) References Cited

U.S. PATENT DOCUMENTS

| 5,004,863 | A | 4/1991 | Umbeck |
| 6,096,950 | A * | 8/2000 | John .................. C07K 14/415 800/314 |
| 6,211,430 | B1 | 4/2001 | John |
| 6,483,013 | B1 | 11/2002 | Reynaerts et al. |
| 7,172,881 | B2 | 2/2007 | Huang et al. |
| 7,626,081 | B2 | 12/2009 | Rathore et al. |
| 2003/0106089 | A1 | 6/2003 | McBride et al. |
| 2013/0081154 | A1 | 3/2013 | Meulewaeter et al. |

FOREIGN PATENT DOCUMENTS

| WO | 9215675 A1 | 9/1992 |
| WO | 9640924 A2 | 12/1996 |
| WO | 0071733 A1 | 11/2000 |
| WO | 2008083969 A2 | 7/2008 |
| WO | 2010015423 A2 | 2/2010 |
| WO | 2012093032 A1 | 7/2012 |
| WO | 2016062615 A1 | 4/2016 |

OTHER PUBLICATIONS

Han et al. (NCBI, GenBank Accession No. GQ406337; Published Sep. 1, 2009.*
Benfey et al., Science 250:959-966, 1990.*
Kim et al., Plant Mol. Biol. 24:105-117, 1994.*
Donald et al., EMBO J. 9:1717-1726, 1990.*
Graves et al. (Journal of Experimental Botany, 39:59-69, 1998).*
Delaney et al. (Plant Cell Physiol., 48:1426-1437, 2007).*
Mehrotra et al. (Plant Mol. Biol., 75:527-536, 2011).*
Basra, Amaritt S., et al., Development of the Cotton Fiber, Int. Rev of Cytology, 1984, pp. 65-113, vol. 89.
Delaney, Sven K., et al., The Fiber Specificity of the Cotton FSItp4 Gene Promoter is Regulated by an AT-Rich Promoter Region and the AT-Hook Transcription Factor GhAT1, 2007, pp. 1426-1437, vol. 48 (10).
Graves, Duane A., et al., Analysis of the Protein Constituency of Developing Cotton Fibres, Journal of Experiemental Botany, 1988, pp. 59-69, vol. 38, No. 198.
Hsu, Chuan-Yu, et al., Analysis of promoter activity of cotton lipid transfer protein gene LTP6 in transgenic tobacco plants, Plant Science, 1999, pp. 63-70, vol. 143.
John, Maliyakal, et al., Metabolic pathway engineering in cotton: Biosynthesis of polyhydroxybutyrate in fiber cells, Proc. Natl. Acad. Sci., Nov. 1996, pp. 12768-12773, vol. 93.
Li, Xue-Bao, et al., Molecular characterization of the cotton GhTUB1 Gene that is preferentially expressed fiber, Plant Physiology, Oct. 2002, pp. 666-674, vol. 130.
Li, Chun-Hong, et al., Isollation of genes preferentially expressed in cotton fibers by cDNA filter arrays and RT-PCT, Plant Science, 2002, pp. 1113-1120, vol. 163.
Li, Xue-Bao, et al., The cottong ACTIN1 Gene is functionally expressed in fibers and participates in fiber elongation, The Plant Cell, Mar. 2005, pp. 859-875, vol. 17.
Liu, Hsi-Chou, et al., Cloning and promoter analysis of the cotton lipid transfer protein gene Ltp3, Biochimica Biophysica Acta, 2000, pp. 106-111, vol. 1487.
Liu, Zongrang, et al., Creation and analysis of a novel chimeric promoter for the complete containment of pollen- and seed-mediated gene flow, Plant Cell Rep, 2008, pp. 995-1004, vol. 27.
Luo, Ming, et al., GhDET2, a steriod 5a-reductaser, plays an important role in cotton fiber cell initiation and elongation, The Plant Journal, 2007, pp. 419-430, vol. 51.

(Continued)

Primary Examiner — Vinod Kumar
(74) Attorney, Agent, or Firm — Brinks Gilson & Lione

(57) ABSTRACT

The present application discloses a recombinant fiber-selective promoter region comprising a DNA molecule comprising a fiber specificity region of a cotton lipid transfer protein gene promoter, operably linked to a DNA molecule comprising a nucleotide sequence having at least 90% sequence identity to a nucleotide sequence of about 500 consecutive nucleotides of the 3' end of the FB8-like 2 promoter and use thereof to increase fiber-selective expression of products of interest in cotton fiber cells.

18 Claims, 7 Drawing Sheets

Specification includes a Sequence Listing.

(56) References Cited

OTHER PUBLICATIONS

Mehrotra, Rajesh, et al., Designer promoter: an artwork of cis engineering, Plant Mol. Biol., 2011, pp. 527-536, vol. 75.

Ramsey, J.C., et al., Ultrastructural Aspects of early stages in cotton fiber elongation, American Journal Botany, 1976, pp. 868-876, vol. 63.

Ruan, Yong-Ling, et al., A Fiberless seed mutation in cotton is associated with lack of fiber cell initiation in ovule epidermis and alterations in sucrose synthase expression and carbon partitioning in developing seeds1, Plant Physiol., 1998, pp. 399-406, vol. 118.

Ruan, Yong-Ling, et al., Pathway and control of sucrose import into initiating cotton fibre cells, Aust. J. Plant Physiol, 2000, pp. 795-800, vol. 27.

Ruan, Yong-Ling, Suppression of sucrose synthase gene expression represses cotton fiber cell initiation, elongation, and seed development, The Plant Cell, Apr. 2003, pp. 952-964, vol. 15.

Shangguan, Xiao-Xia, et al., Promoter of a cotton fibre MYB gene functional in trichomes of *Arabidopsis* and glandular trichomes of tobacco, Journal of Experimental Botany, 2008, pp. 3533-3542, vol. 59, No. 13.

Song, Ping, et al., Expression of two tissue-specific promoters in transgenic cotton plants, The Journal of Cotton Science, 2000, pp. 217-223, vol. 4.

Stewart, James, Fiber initiation of the cotton ovule (*Gossypium hirsutum*), American Journal of Botany, 1975, pp. 723-730, vol. 62.

Wang, Shui, et al., Control of plant trichome development by a cotton fiber MYB gene, The Plant Cell, Sep. 2004, pp. 2323-2334, vol. 16.

Wu, Aimin, Analysis of the cotton E6 promoter, Tsinghua Science and Technology, Aug. 2005, pp. 409-413, vol. 10, No. 4.

Written Opinion of the International Searching Authority for PCT/EP2015/073931, dated Oct. 15, 2015.

Decision on Appeal dated Sep. 16, 2008 for Ex parte Gregory R. Heck et al., Appeal No. 2008-2875, U.S. Appl. No. 10/925,392.

\* cited by examiner

```
AAGCTTAAAATCACTTATCAATTTCAAAAACAGAGGTTAGCCGAATGCTAAGAGCTTAAA
AATGGCTTCTTTTGTTTCTTTTCTTGCAAACGGTGGAGAGAAGAATAATGAAGATTG
ACCATATCTTTTTTATTATGTTTAACATATAATATTAATAATTAATCATAATTATAC
TTTGGTGAATGTGACAGTGGGGATATACGTAAAGTATATAACATTATACTTTTTGCAAGC
AGTTGGCTGGTCTACCCAAGAGTGATCAAATTTTGAGCTGCCTTCAATGAGCCAATTTTT
GCCTATAATGGATAAAGGCACTTTGTCTAGTTCAACTGCTCACAGAATAATGTTAAAATG
AAATTAAAACAAGGTGGGCTGGTCACACCAAAAATAAAATATTAATGTGGTGTTTGGT
TAGTCGATTTTATATTAGTTCCATGGCATACCGCCCTGGAAAAGGAAAATTCATGTAAATA
ATATATTTATAAAAATTTATATATTAAAACTAAAATGAAATTTTAGTTGAAATAGTTAAGTTA
AAAAGAGTAAAATTTATAATTTATCATAATTTATAGAAATTGAGACTAAAAACATTAA
GAGAATAAATTCTATAACAAAGACAATTTAGTAAAATGTCCTTTTAGGTAATTTTAAGT
ACTCTTAACCAAATAAAAAATTCAAATCAAATTAACCAAATAAGATATATAACATACG
GAACATCCCACTTATATCTTCACATCCCCGTAATCTTATTATGAAAAGTAATCTTATATT
ACTCGAATCAAATGCTCTCCACAAACTATTATCTAAATAAAGAAAAACACTTAATTTTTAT
AACATTTTTTCATATATTTGAAAGATTATATTTTGTATTTTACGTAAAAATATTTGA
CATAGATTGAGCACCTTTTTAACATAATTCCACCATAAGTCAATTATGTAGATGAGAAAT
TGGTACAAACAACGTGGAGCCAAATCCCACCAAACCATCTCATCCTCCCTATAAAG
GCTTGCTACACATAGACAACAATCCACACAAAATACACTTAAAATTCTTTTCTTCTAT
TTGGTTAACC
```

Figure 1

```
FB8-like 2       1 AAGCTTAAAATCACTTATCAATTTCAAAAACAGAGGTTAGCCGAATGCTAAGAGCTTAAAAATGGCTTCT
FB8-like 2_FSR   1 AAGCTTAAAATCACTTATCAATTTCAAAAACAGAGGTTAGCCGAATGCTAAGAGCTTAAAAATGGCTTCT FB8-like 2      71 TTTGTTTCTTTTTCTTGCAAACGGTGGAGAGAGGGAAATGAAGATTGACCATATCTTTTTTATTAT
FB8-like 2_FSR  71 TTTGTTTCTTTTTCTTGCAAACGGTGGAGAGAGGGAAATGAAGATTGACCATATCTTTTTTATTAT FB8-like 2     141 GTTTTAACATATATAATTATTAATTAATCATAATTATACTTTGGTGAATGTGACAGTGGGATATACGT
FB8-like 2_FSR 141 GTTTTAACATATATAATTATTAATTAATCATAATTATACTTTGGTGAATGTGACAGTGGGATATACGT FB8-like 2     211 AAAGTATATAACATTATACTTTTTGCAAGCAGTTGGCTGTCTACCCAAGAGTGATCAAATTTTGAGCTG
FB8-like 2_FSR 211 AAAGTATATAACATTATACTTTTTGCAAGCAGTTGGCTGTCTACCCAAGAGTGATCAAATTTTGAGCTG FB8-like 2     281 CCTTCAATGAGCCAATTTTTGCCTATAATGGATAAAGGCACTTTGTCTAGTTCAACTGCTCACAGAATAA
FB8-like 2_FSR 281 CCTTCAATGAGCCAATTTTTGCCTATAATGGATAAAGGCACTTTGTCTAGTTCAACTGCTCACAGAATAA FB8-like 2     351 TGTTAAAATGAAATTAAAACAAGGTGGGCTGGTCACACCAAAAAATAAAATATTAATGTGGTGTTTGGT
FB8-like 2_FSR 351 TGTTAAAATGAAATTAAAACAAGGTGGGCTGGTCACACCAAAAAATAAAATATTAATGTGGTGTTTGGT FB8-like 2     421 TAGTCG--------------------------------------------------------------
FB8-like 2_FSR 421 TAGTCGGATTTTTATATTAGTTCCATGGCATACCGCCTGGAAAAGGAAAATTCATGTAAATATATTTAT FB8-like 2     427 --------------------------------------------------------------AAT
FB8-like 2_FSR 491 AAAAATTTATATTAAAACTAAATGAAATTTAGTTGAAATAGTTAAGTTAAAAAGAGTAAAATTTATAAT FB8-like 2     430 TTATCATAATTTTATAGAAATTGAGACTAAAAAACATTAAGAGAATAAAATTCTATAACAAAGACAATTTA
FB8-like 2_FSR 561 TTATCATAATTTTATAGAAATTGAGACTAAAAAACATTAAGAGAATAAAATTCTATAACAAAGACAATTTA FB8-like 2     500 GTAAAAATGTCCTTTTAGGTAATTTTAAGTACTCTTAACCAAAATAAAAAATTCAAATTAACCAA
FB8-like 2_FSR 631 GTAAAAATGTCCTTTTAGGTAATTTTAAGTACTCTTAACCAAAATAAAAAATTCAAATTAACCAA FB8-like 2     570 ATAAGATAATAATAACATACGGAACATCCCACTTATAATCTTACATCCCGTAATCTTATTATGAAAAGTA
FB8-like 2_FSR 701 ATAAGATAATAATAACATACGGAACATCCCACTTATAATCTTACATCCCGTAATCTTATTATGAAAAGTA
```

Figure 2

```
FB8-like 2      640  ATCTTATATTACTCGAATCAAATGCTCTCACAAACTATTATCTAAATAAAGAAAAACACTTAATTTTTAT
FB8-like 2_FSR  771  ATCTTATATTACTCGAATCAAATGCTCTCACAAACTATTATCTAAATAAAGAAAAACACTTAATTTTTAT FB8-like 2      710  AACATTTTTTTCATATATATTTGAAAGATTATATTTGTATTTTTACGTAAAAATATTTGACATAGATTGA
FB8-like 2_FSR  841  AACATTTTTTTCATATATATTTGAAAGATTATATTTGTATTTTTACGTAAAAATATTTGACATAGATTGA FB8-like 2      780  GCACCTTTTTAACATAATTCCACCATAAGTCAATTATGTAGATGAGAAATTGGTACAAACAACGTGGAGC
FB8-like 2_FSR  911  GCACCTTTTTAACATAATTCCACCATAAGTCAATTATGTAGATGAGAAATTGGTACAAACAACGTGGAGC FB8-like 2      850  CAAATCCCACCAAACCATCTCTCATCCTCCTATAAAAGGCTTGCTACACATAGACAACAATCCACACA
FB8-like 2_FSR  981  CAAATCCCACCAAACCATCTCTCATCCTCCTATAAAAGGCTTGCTACACATAGACAACAATCCACACA FB8-like 2      920  AAAATACACTTAAAATTCTTTTCTTTTCTATTTGGTTAACC
FB8-like 2_FSR  1051 AAAATACACTTAAAATTCTTTTCTTTTCTATTTGGTTAACC
```

```
4-4 (Fblate)  3114  agttcaactgctcacagaataatgttaaaatgaattaaaataaggtggcctggtcacacacaca---aa
Fblate2       1373  agttcaactgctcacagaataatgttaaaatgaattaaaataaggtggcctggtcacacacaca---aa
Fb8-like-1     387  agttcaactgctcacagaataatgttaaaatgaattaaaataaggtggcctggtcacacacaca---aa
Fb8-like-2     328  agttcaactgctcacagaataatgttaaaatgaattaaaacaaggtgggctggtcacac-caaaaaaat 4-4 (Fblate)  3181  aaaaaactaatgt-tggttggttgaatttttatattacggaatgtaatatatttaaaataaaattat
Fblate2       1443  aaaaaactaatgt-tggttggttgaatttttatattacggaatgtaatatatttaaaataaaattat
Fb8-like-1     454  aaaaaactaatgt-tggttggttgaatttttatattacggaatgtaatatatttaaaataaaattat
Fb8-like-2     398  aaaatattaatgtgtggtgtttggtt----------------------agtcga------------

4-4 (Fblate)  3250  gttatttagattcttaatattttggagcattccatactataattcgta-acataatattaaaa-atagt
Fblate2       1512  gttatttagattcttaatatttt-gagcattccatactataatctcgtatacataatattaaaatagt
Fb8-like-1     523  gttatttagattcttaatatttg-agcattccataataattcgtataacataattaaaatatagt
Fb8-like-2          --------------------------------------------------------

4-4 (Fblate)  3319  aatataaagtgtaattaacttaaattacaagcataatatttgaatcaattaattttatttct
Fblate2       1581  aatataaagtgtaattaacttaaattacaagcataatatttgaatcaattaattttatttct
Fb8-like-1     592  aatataaagtgtaattaacttaaattacaagcataatatttgaatcaattaattttatttct
Fb8-like-2          --------------------------------------------------------

4-4 (Fblate)  3389  attattttaattaattagtctatttttcaaaataaattaaatctaaataaataatttcctta
Fblate2       1651  attattttaattaattagtctatttttcaaaataaattaaatctaaataaataatttcctta
Fb8-like-1     662  attattttaattaattagtctattttttcaaaattaaatctaaataaaataatttcctta
Fb8-like-2          --------------------------------------------------------

4-4 (Fblate)  3459  atgttgaacaactcatgttatacttcaaaattataagtattatatttaccttgatgatttattattag
Fblate2       1721  a---------------------------------------------------------
Fb8-like-1     732  atgtgaacaactcatgttatacttcaaaattataagtattatatttaccttgatgatttattattag
Fb8-like-2          --------------------------------------------------------
```

RECOMBINANT PROMOTER WITH INCREASED FIBER-SPECIFIC EXPRESSION

CROSS REFERENCE TO RELATED APPLICATIONS

This application is a national stage application under 35 U.S.C. § 371 of PCT Application No. PCT/EP15/073931, filed Oct. 15, 2015, which claims the benefit of European Patent Application Serial No. 14189642.3, filed Oct. 21, 2014, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "BCS14-2010-ST25.txt," created on Sep. 26, 2014, and having a size of 31 kilobytes and is filed concurrently with the specification. The sequence listing contained in this ASCII formatted document is part of the specification and is herein incorporated by reference in its entirety.

FIELD OF THE INVENTION

The invention relates to plant molecular biology and agronomy. Materials and methods are described to express a gene of interest preferentially or selectively in fibers of plants, such as cotton plants. In particular, the invention provides novel recombinant or chimeric promoters, promoter regions and expression cassettes with enhanced fiber selectivity, which can be used for achieving fiber-preferential or fiber-selective expression in cotton plants.

BACKGROUND

Cotton fiber is the single most important textile worldwide. About 80 million acres of cotton are harvested annually across the globe. Cotton is the fifth largest crop in the U.S. in terms of acreage production, with an average of 10.3 million acres planted in the years 2006 to 2008. About 90% of cotton grown worldwide is *Gossypium hirsutum* L., whereas *Gossypium barbadense* accounts for about 8%. Consequently, the modification of cotton fiber characteristics to better suit the requirements of the industry and the consumer is a major effort in breeding by either classical methods or by genetically altering the genome of cotton plants. Goals to be achieved include increased lint fiber length, strength, dyeability, fiber maturity ratio, fiber uniformity, decreased fuzz fiber production, immature fiber content, and micronaire.

Cotton fiber development is a multistage process under the regulation of a vast number of genes, many of which are up-regulated or highly expressed in developing fiber cells (Li, C. H. et al. 2002, Plant Sci 163: 1113-1120; Ruan et al. 2003, Plant Cell 15: 952-964; Wang et al. 2004, Plant Cell 16: 2323-2334; Li et al. 2005, Plant Cell 17: 859-875; Luo et al. 2007, Plant Journal 51: 419-430).

Each cotton fiber is a differentiated single epidermal cell that initiates from the epidermis of the outer integument of the ovule. Approximately half a million fibers are produced per cotton boll, some forming fuzz and some forming lint. Differentiation of an epidermal cell into a fiber requires a change in cell fate, which is a fundamental biological process involving genetic, physiological and developmental "switches". However, only ~25-30% of the epidermal cells differentiate into the commercially important lint fibers. The majority of cells do not differentiate into fibers or develop into short fibers or fuzz. Genetic mutations, polyploidy, pollination/fertilization and hormonal regulation can affect the number of cells developing into fibers or alter fiber cell properties (fuzz vs. lint).

The development of cotton fibers starts on the day of anthesis (flowering) and is divided into four distinct but overlapping phases: fiber cell initiation which starts immediately after anthesis and lasts up to 3 days post anthesis (DPA), elongation (3 till 20 DPA), secondary wall biosynthesis (15-35 DPA) and maturation (45-60 DPA) (Basra & Malik 1984, Int Rev of Cytology 89: 65-113; Graves and Stewart, 1988, J. Exp. Bot. 39 (1): 59-69; Ramsey and Berlin, 1976, American Journal of Botany 63 (6): 868-876; Ruan and Chourey, 1998, Plant Physiology 118: 399-406; Ruan et al. 2000, Aust. J. Plant Physiol. 27:795-800; Stewart, 1975, Am. J. Bot. 62, 723-730). The first three stages occur while the fiber cell is alive and actively growing whereas maturation occurs after opening of the boll containing the white fluffy fibers and describes the drying of the mature fibers.

These developmental phases are regulated by the ordered expression of a multiplicity of genes in the fiber cell, a proportion of which is fiber specific and therefore thought to play a major role during fiber development. The promoters of fiber specific genes may regulate gene function by restricting transcription to the fiber cell (Delaney et al. 2007, Plant Cell Physiol. 48(10): 1426-1437).

Various promoters controlling or regulating the expression of such fiber-preferential or fiber-specific genes have been described and also have been exploited to genetically modify fiber characteristics.

E6 was the first cotton fiber gene identified, and the E6 promoter has been used for engineering cotton fiber quality (John and Keller 1996, PNAS 93: 12678-12773). GhRDL1, a gene highly expressed in cotton fiber cells at the elongation stage, encodes a BURP domain containing protein (Li, C. H. et al. 2002, ibid.), and the GaRDL1 promoter exhibited a trichome-specific activity in transgenic Arabidopsis plants (Wang et al. 2004, ibid.). GhTUB1 transcripts preferentially accumulate at high levels in fiber, accordingly, the pGh-TUB1::GUS fusion gene was expressed at a high level in fiber but at much lower levels in other tissues (Li, X. B. et al. 2002, Plant Physiol. 130(2): 666-74). Promoters of three cotton lipid transfer protein genes, LTP3, LTP6, and FSltp4, were able to direct GUS gene expression in leaf and stem glandular secretory trichomes (GSTs) in transgenic tobacco plants (Hsu et al. 1999, Plant Science 143: 63-70; Liu et al. 2000, ibid.; Delaney et al. 2007, Plant and Cell Physiol. 48: 1426-1437).

The cotton R2R3 MYB transcription factor GaMYB2 has been shown to be a functional homologue of Arabidopsis GLABRA1 (GL1), a key regulator of Arabidopsis trichome formation. GaMYB2 is expressed in cotton fiber cells at the early developmental stages (Wang, S. et al., 2004, ibid.). Its promoter drives trichome-specific expression also in Arabidopsis and GST headspecific expression in tobacco (Shangguan et al. 2008, J. Exp Botany 59(13): 3533-3542).

U.S. Pat. No. 7,626,081 discloses a cotton seed-specific promoter found in the alpha globulin gene. The promoter Gh-sp is derived from a seed protein gene and is active only in maturing cotton seeds (Song et al. 2000, Journal Cotton Science 4: 217-223).

U.S. patent application 2003/0106089 discloses a gene expressed in a fiber-specific manner and its promoter which is active particularly in very early fiber development.

U.S. Pat. No. 6,211,430, U.S. patent application 2013/0081154, EP patent application Ser. No. 13/189,991, U.S. Pat. No. 6,096,950 and WO 96/40924 disclose promoters derived from members of a multigene family in cotton which all direct expression during late fiber development.

Despite the fact that many promoters known to drive seed-preferential or fiber-preferential expression in cotton plants are available in the art, these promoters may drive expression of associated genes of interest in cotton tissue other than fiber (initiation) cells, potentially resulting in cytotoxicity and low transformation efficiencies. Therefore, a need remains for fiber-preferential or fiber-selective promoters with the capacity to control transcription in developing fiber cells, preferably in a more selective manner. These and other problems are solved as described hereinafter in the summary, detailed embodiments, examples, drawings and claims.

SUMMARY OF THE INVENTION

In a first embodiment, a recombinant DNA molecule is provided which comprises in order:
  a. a DNA molecule comprising a fiber specificity region of a cotton lipid transfer protein gene promoter, such as a fiber specificity region comprising a nucleotide sequence having at least 90% sequence identity to the nucleotide sequence of SEQ ID No. 4, or comprising the nucleotide sequence of SEQ ID No. 4, or comprising the nucleotide sequence of SEQ ID No. 3; operably linked to
  b. a DNA molecule comprising a nucleotide sequence having at least 90% sequence identity to a nucleotide sequence of about 500 consecutive nucleotides of the 3' end of the FB8-like 2 promoter of SEQ ID No. 2 wherein that nucleotide sequence may be selected from the following group: the nucleotide sequence of SEQ ID No. 2 from the nucleotide at position 427 to the nucleotide at position 922, the nucleotide sequence of SEQ ID No. 2 from the nucleotide at position 427 to the nucleotide at position 926, the nucleotide sequence of SEQ ID No. 2 from the nucleotide at position 427 to the nucleotide at position 959, the nucleotide sequence of SEQ ID No. 5 from the nucleotide at position 911 to the nucleotide at position 1405, the nucleotide sequence of SEQ ID No. 5 from the nucleotide at position 911 to the nucleotide at position 1409, the nucleotide sequence of SEQ ID No. 5 from the nucleotide at position 911 to the nucleotide at position 1437, the nucleotide sequence of SEQ ID No. 6 from the nucleotide at position 3638 to the nucleotide at position 4132, the nucleotide sequence of SEQ ID No. 6 from the nucleotide at position 3638 to the nucleotide at position 4136, the nucleotide sequence of SEQ ID No. 6 from the nucleotide at position 3638 to the nucleotide at position 4164, the nucleotide sequence of SEQ ID No. 7 from the nucleotide at position 1781 to the nucleotide at position 2276, the nucleotide sequence of SEQ ID No. 7 from the nucleotide at position 1781 to the nucleotide at position 2280, or the nucleotide sequence of SEQ ID No. 7 from the nucleotide at position 1781 to the nucleotide at position 2314.

In a further embodiment, the recombinant DNA molecule comprises a DNA molecule comprising a nucleotide sequence having at least 90% sequence identity to a nucleotide sequence of about 400 consecutive nucleotides of the 5' end of the FB8-like 2 promoter of SEQ ID No 2 preceding the DNA molecule comprising the fiber specificity region, wherein the DNA molecule comprising a nucleotide sequence having at least 90% sequence identity to a nucleotide sequence of about 400 consecutive nucleotides of the 5' end of the FB8-like 2 promoter of SEQ ID No 2 may be selected from the nucleotide sequence of SEQ ID No 5 from the nucleotide at position 61 to the nucleotide at position 475, the nucleotide sequence of SEQ ID No 5 from the nucleotide at position 61 to the nucleotide at position 732, the nucleotide sequence of SEQ ID No 6 from the nucleotide at position 2787 to the nucleotide at position 3202, the nucleotide sequence of SEQ ID No 6 from the nucleotide at position 2787 to the nucleotide at position 3459, the nucleotide sequence of SEQ ID No 7 from the nucleotide at position 1047 to the nucleotide at position 1464, the nucleotide sequence of SEQ ID No 7 from the nucleotide at position 1047 to the nucleotide at position 1721.

In yet another embodiment, the recombinant DNA molecule comprises a nucleotide sequence having about 90% sequence identity to the nucleotide sequence of SEQ ID No. 1 from the nucleotide at position 1 to the nucleotide at position 1053, such as the nucleotide sequence of SEQ ID No. 1 from the nucleotide at position 1 to the nucleotide at position 1053, the nucleotide sequence of SEQ ID No. 1 from the nucleotide at position 1 to the nucleotide at position 1057 or the nucleotide sequence of SEQ ID No. 1 from the nucleotide at position 1 to the nucleotide at position 1090.

The recombinant DNA molecules here above described are promoters or promoter regions promoting fiber-selective expression of a coding region operably linked thereto, wherein the fiber-selective expression may be increased compared to a FB8-like 2 promoter.

It is also an object of the invention to provide chimeric genes or recombinant DNA molecules comprising the following operably linked DNA regions:
  a. a promoter or promoter region comprising a recombinant DNA molecule as hereinabove described;
  b. a DNA encoding a biologically active RNA molecule; and optionally
  c. a transcription termination region or a transcription termination and polyadenylation region.

The invention also provides cotton plant cells or cotton plants comprising a recombinant DNA molecule having fiber selective promoter activity or a chimeric gene as herein described, as well as fibers obtainable from such cotton plants.

In yet another embodiment, a method for making a transgenic cotton plant cell or plant is provided comprising the step of providing a cell of a cotton plant with a recombinant DNA molecule as herein described and optionally regenerating a cotton plant from said cotton plant cell.

The invention further provides a method for increasing the selectivity of expression of a biologically active RNA in fiber cells of a cotton plant comprising providing cells of such cotton plant with a chimeric gene comprising a recombinant fiber selective promoter as herein described.

Yet another object of the invention is to provide use of a recombinant fiber-specific promoter as herein described to express a biologically active RNA selectively in fiber cells of a cotton plant.

BRIEF DESCRIPTION OF THE DRAWINGS

FIG. 1: Nucleotide sequence of the recombinant promoter region FB8-like2_FSR. The nucleotide sequence in normal font corresponds to the nucleotide sequence of the FB8-like2 fiber-selective promoter region. The nucleotides indicated in bold correspond to a portion of the fiber specific promoter of a cotton lipid transfer protein gene (FDSltp4; Delaney et al. 2007, Plant and Cell Physiol. 48: 1426-1437) comprising an AT-rich 84 bp fiber specificity region (FSR), indicated in bold, italic font which is underlined. The nucleotide sequence correspond to SEQ ID No. 1.

FIG. 2: Comparison of the nucleotide sequences of the FB8-like2 promoter region (SEQ ID No. 2) and the recombinant promoter region FB8like2_FSR (SEQ ID No. 1).

Figure 3:
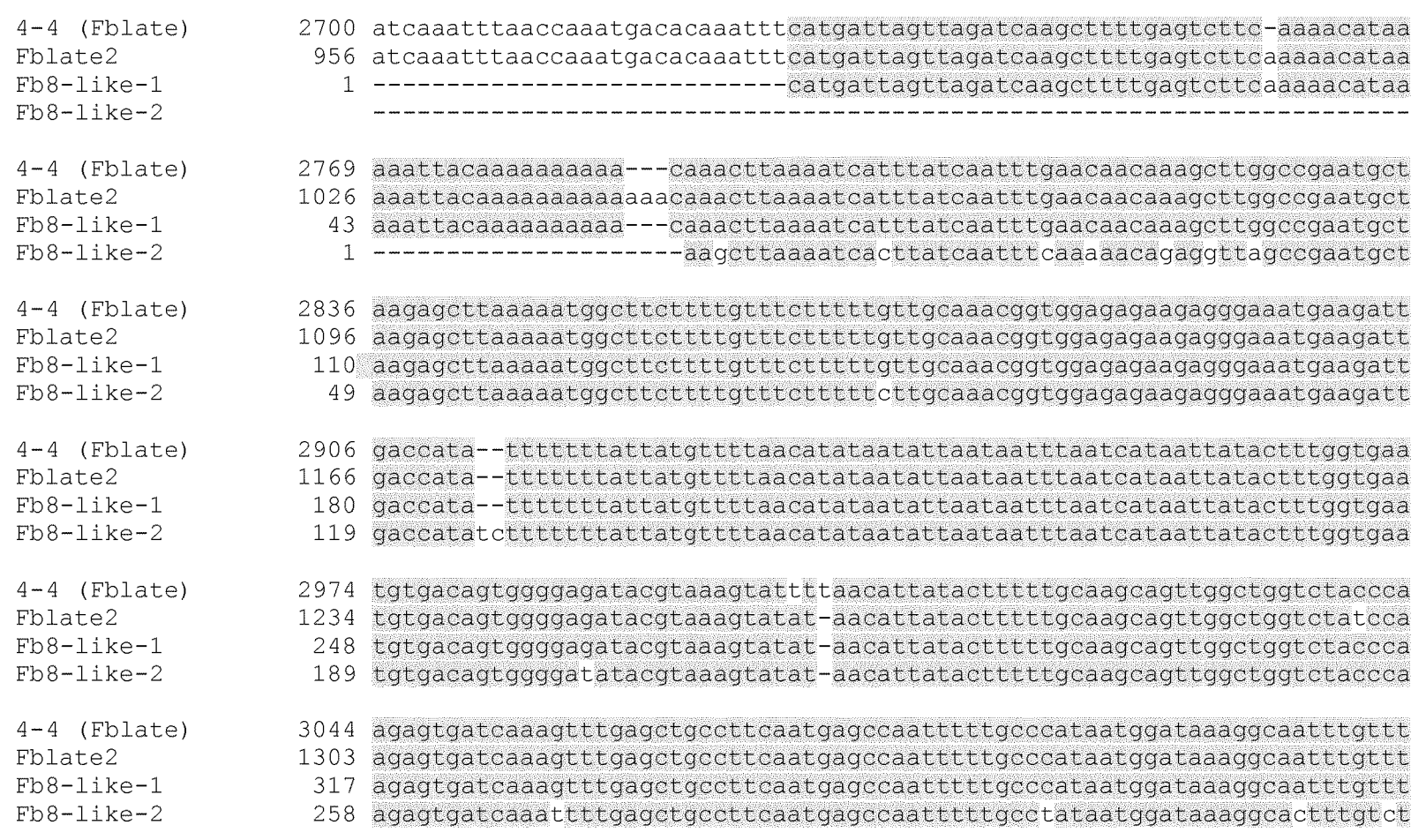
Figure 3:
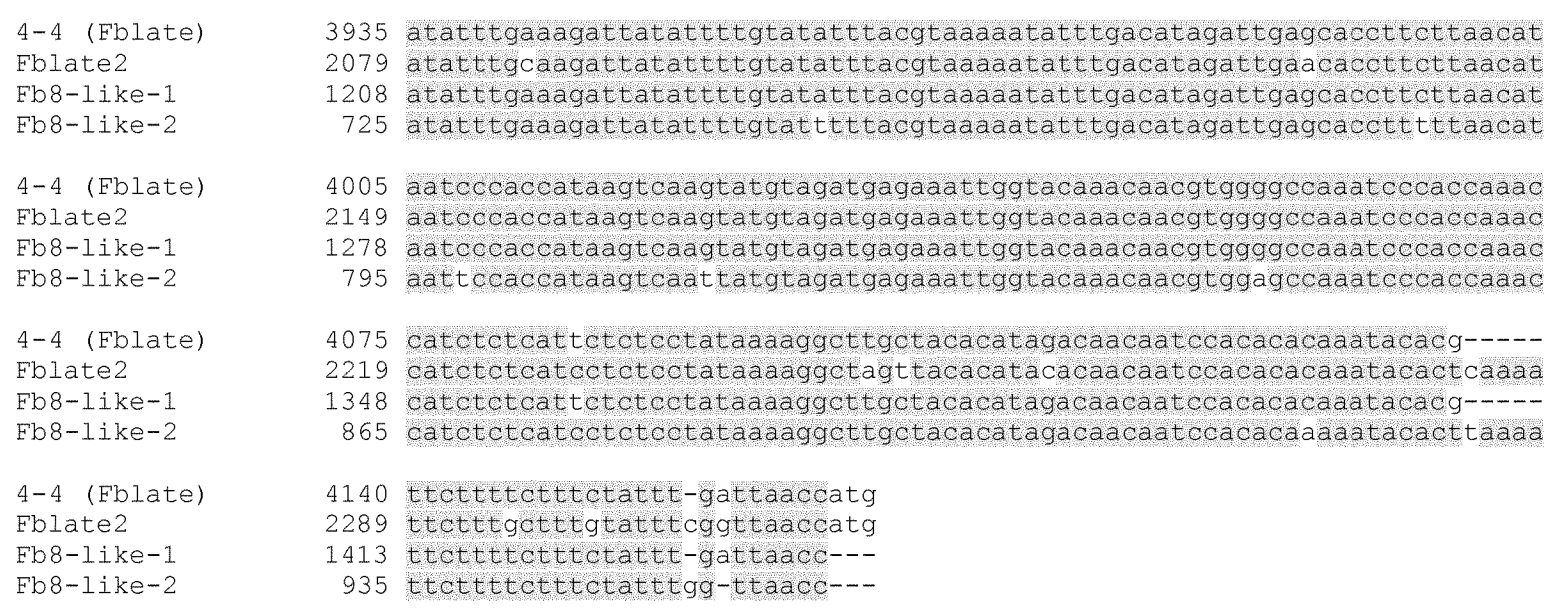

FIG. 3: Comparison of the nucleotide sequences of the fiber specific promoter region of Fblate (4-4) described in patent application WO96/40924 and represented in the sequence listing as SEQ ID No. 6; the fiber specific promoter region of Fblate2, described in patent U.S. Pat. No. 6,211,430 and represented in the sequence listing as SEQ ID No. 7: the fiber specific promoter region of FB8-like1, described in patent application 2013/0081154 and represented in the sequence listing as SEQ ID No. 5; and the fiber specific promoter region of FB8-like2, described in patent application EP13189991 and represented in the sequence listing as SEQ ID No. 2.

DETAILED DESCRIPTION

In this specification, a number of documents including patent applications and manufacturer's manuals are cited. The disclosure of these documents, while not considered relevant for the patentability of this invention, is hereby incorporated by reference in its entirety. More specifically, unless indicated otherwise, all referenced documents are incorporated by reference to the same extent as if each individual document was specifically and individually indicated to be incorporated by reference.

The sequence listing that is contained in the file named BCS14-2010_ST25.txt, which is 32 kilobytes (measured in MS windows operating system), comprises sequences 1 to 8 and was created on Sep. 26, 2014, is filed herewith and incorporated herein by reference.

As used herein, the term "comprising" is to be interpreted as specifying the presence of the stated features, integers, steps or components as referred to, but does not preclude the presence or addition of one or more features, integers, steps or components, or groups thereof. Thus, e.g., a nucleic acid comprising a sequence of nucleotides, may comprise more nucleotides than the actually cited ones, i.e., be embedded in a larger nucleic acid. A chimeric gene as will be described further below which comprises a nucleic acid which is functionally or structurally defined may comprise additional nucleic acids etc. However, in context with the present disclosure, the term "comprising" also includes "consisting of". In other words, the terminology relating to a nucleic acid "comprising" a certain nucleotide sequence, as used throughout the text, refers to a nucleic acid or protein including or containing at least the described sequence, so that other nucleotide or amino acid sequences can be included at the 5' (or N-terminal) and/or 3' (or C-terminal) end, e.g. (the nucleotide sequence of) a selectable marker protein, (the nucleotide sequence of) a transit peptide, and/or a 5' leader sequence or a 3' trailer sequence.

The current invention is based on the unexpected finding that inclusion of a fiber specificity region derived from the promoter of the cotton gene encoding the cotton lipid transfer protein Fsltp4, into the promoter of the FB8like2-gene (SEQ ID No. 2), which drives expression in a fiber-selective manner, increases the fiber selective expression of the recombinant promoter. This can be observed in particular by comparing the transformation frequencies obtained with a vector comprising a chitin-synthase gene and a glutamine:fructose-6-phosphate amidotransferase under control of such recombinant promoter, to the transformation frequencies obtained with a vector comprising the same gene but under control of the promoter of the FB8 like2-gene.

In one aspect, the present application discloses a recombinant DNA molecule comprising, in order, a DNA molecule comprising a fiber specificity region of a cotton lipid transfer protein gene promoter, operably linked to a DNA molecule comprising a nucleotide sequence having at least 90% sequence identity to a nucleotide sequence of about 500 consecutive nucleotides of the 3' end of the FB8-like 2 promoter of SEQ ID No 2.

In another aspect, the recombinant DNA molecule may further comprise a DNA region comprising a nucleotide sequence having at least 90% sequence identity to a nucleotide sequence of about 400 consecutive nucleotides of the 5' end of the FB8-like 2 promoter of SEQ ID No 2, which precedes the DNA molecule comprising the fiber specificity region.

As demonstrated in FIG. 3, the nucleotide sequences of the fiber selective promoter regions of the FB8-like2 gene, the FB8-like1 gene, the Fblate (4-4) and the Fblate2 gene share a high degree of nucleotide sequence identity (90% or more) in the region just upstream of the initiation codon ATG, between nucleotide positions 427-959 of FB8-like2 promoter region (SEQ ID 1; corresponding to the nucleotide positions 558-1090 in FB8-like2_FSR recombinant promoter region of SEQ ID No. 2), between nucleotide positions 913-1437 of FB8-like1 promoter region (SEQ ID No. 5), between nucleotide positions 3640-4164 of the Fblate promoter region (SEQ ID No. 6) or between nucleotide positions 1783-2314 of the FBlate2 promoter region (SEQ ID No. 7) and it is expected that these regions can be exchanged for each other.

Accordingly, in yet another aspect, the DNA region of the recombinant DNA molecule which comprises a nucleotide sequence having at least 90% sequence identity to a nucleotide sequence of about 500 consecutive nucleotides of the 3' end of the FB8-like 2 promoter region of SEQ ID No 2 may be selected from the nucleotide sequence of SEQ ID No. 1 from the nucleotide at about position 558 to the nucleotide at position 1090, the nucleotide sequence of SEQ ID No. 2 from the nucleotide at position 427 to the nucleotide at about position 959, the nucleotide sequence of SEQ ID No. 5 from the nucleotide at about position 913 to the nucleotide at position 1437, the nucleotide sequence of SEQ ID No. 6 from the nucleotide at position 3640 to the nucleotide at position 4164, or the nucleotide sequence of SEQ ID NO. 7 from the nucleotide at position 1783 to the nucleotide position 2314.

It has also been observed that transcription controlled by the FB8-like2 promoter can be initiated at position 922 or position 926 of SEQ ID No. 2 corresponding to positions 1053 and 1057 respectively of SEQ ID No. 1 or positions 1405 and 1409 respectively of SEQ ID No. 5, or positions 4132 and 4136 respectively of SEQ ID No. 6 or positions 2276 and 2280 respectively of SEQ ID No. 7. Thus, recombinant promoters may comprise at their 3'end a nucleotide selected from the nucleotide sequence of SEQ ID No. 2 from position 427 to position 922, or from position 427 to position 926, the nucleotide sequence of SEQ ID No. 5 from position 913 to position 1405, or from position 913 to position 1409, the nucleotide sequence of SEQ ID No. 6 from position 3640 to position 4132, or from position 3640 to position 4136, and the nucleotide sequence of SEQ ID No. 7 from position 1783 to position 2276, or from position 1783 to position 2280.

As also demonstrated in FIG. 3, the nucleotide sequences of the fiber selective promoter regions of the FB8-like2 gene, the FB8-like1 gene, the Fblate (4-4) and the Fblate2 gene share a high degree of nucleotide sequence identity (90% or more) in their nucleotide sequence corresponding to the 5' region of the FB8-like 2 promoter or promoter region, between nucleotide positions 1-426 of FB8-like2 promoter region (SEQ ID 1; corresponding to the nucleotide positions 1-426 in FB8-like2_FSR recombinant promoter region of SEQ ID No. 2), between nucleotide positions 61-475 of FB8-like1 promoter region (SEQ ID No. 5), between nucleotide positions 2787-3202 of the Fblate promoter region (SEQ ID No. 6) or between nucleotide positions 1047-1464 of the FBlate2 promoter region (SEQ ID No. 7) and it is expected that also these regions can be exchanged for each other.

The fiber specificity region of the cotton FTLSp4 gene promoter is an AT-rich region which interacts with the AT-Hook transcription factor GhAT1. Suitable fiber specificity regions comprise a nucleotide sequence having at least 90% or 95% sequence identity or are identical to the nucleotide sequence of SEQ ID No. 4, such as the nucleotide sequence of SEQ ID No. 3.

A particular embodiment of the invention is the recombinant DNA molecule comprising the nucleotide sequence of SEQ ID No. 1 form the nucleotide at position 1 to the nucleotide at position 1053, the nucleotide sequence of SEQ ID No. 1 form the nucleotide at position 1 to the nucleotide at position 1057 or the nucleotide sequence of SEQ ID No. 1 form the nucleotide at position 1 to the nucleotide at position 1090.

Also provided are a fiber-selective promoter DNA comprising a nucleotide sequence having at least 95%, at least 96%, at least 97%, at least 98%, at least 99% sequence identity with or being identical to the nucleotide sequence of SEQ ID No. 1 between nucleotide position 1 and 1053 or having at least 95%, at least 96%, at least 97%, at least 98%, at least 99% sequence identity with or being identical to the nucleotide sequence of SEQ ID No. 1 between nucleotide position 1 and 1057, or a fiber-preferential promoter having at least 95%, at least 96%, at least 97%, at least 98%, at least 99% sequence identity with or being identical to the nucleotide sequence of SEQ ID No. 1 between nucleotide position 1 and 1090 and which have fiber-selective promoter activity.

The isolated nucleic acids of this aspect are hereinafter also referred to as "promoter" or "promoter region".

Methods of evaluating whether a nucleic acid sequence as described above, which in the present application represents a promoter sequence, is capable of inducing expression of a chimeric gene it is comprised in or, in particular, of a nucleic acid sequence operably linked thereto, in a fiber-preferential manner are known to the skilled person.

For example reporter gene studies may be performed in order to evaluate the expression inducing function of a nucleic acid sequence. This includes operably linking the nucleic acid sequence of the invention to a reporter gene such as GUS, introducing the resulting nucleic acid construct in a plant or plant cell, such as in a cotton plant, and evaluating induction of the expression of said reporter gene in different tissues of said plant, as will also be described in more details further below.

As used herein, the term "promoter" denotes any nucleic acid sequence, such as a DNA sequence, which is recognized and bound (directly or indirectly) by a DNA-dependent RNA-polymerase during initiation of transcription, resulting in the generation of an RNA molecule that is complementary to the transcribed DNA. This region may also be referred to as a "5' regulatory region". Promoters are usually located upstream of the 5' untranslated region (UTR) preceding the protein coding sequence to be transcribed and have regions that act as binding sites for RNA polymerase II and other proteins such as transcription factors to initiate transcription of an operably linked sequence. Promoters may themselves contain sub-elements (i.e. promoter motifs) such as cis-elements or enhancer domains that regulate the transcription of operably linked genes. The promoter and a connected 5' UTR are also referred to as "promoter region".

Confirmation of promoter activity for a promoter sequence or a functional promoter fragment or promoter region may be determined by those skilled in the art, for example using a promoter-reporter construct comprising the promoter sequence operably linked to an easily scorable marker as herein further explained. The fiber-preferential expression capacity of the identified or generated fragments or variants of the promoter described herein can be conveniently tested by operably linking such nucleic acid sequences to a nucleotide sequence encoding an easily scorable marker, e.g. a beta-glucuronidase gene, introducing such a chimeric gene into a plant and analyzing the expression pattern of the marker in fiber cells as compared to the expression pattern of the marker in other parts of the plant. Other candidates for a marker (or a reporter gene) are chloramphenicol acetyl transferase (CAT), beta-galactosidase (beta-GAL), and proteins with fluorescent or phosphorescent properties, such as green fluorescent protein (GFP) from Aequora victoria or luciferase. To confirm promoter function, a nucleic acid sequence representing the promoter is operably linked to the coding sequence of a marker (reporter) gene by recombinant DNA techniques well known in the art. The reporter gene is operably linked downstream of the promoter, so that transcripts initiating at the promoter proceed through the reporter gene. The expression cassette containing the reporter gene under the control of the promoter can be introduced into an appropriate cell type by transformation techniques well known in the art and described elsewhere in this application. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography. The level of enzyme activity corresponds to the amount of enzyme that was made, which in turn reveals the level of expression and the fiber-preferential functionality of the promoter or fragment or variant thereof. This level of expression can also be compared to other promoters to determine the relative strength of the promoter under study. Once activity and functionality is confirmed, additional mutational and/or deletion analyses may be employed to determine e.g. a minimal promoter region and/or sequences required to initiate transcription. Thus, sequences can be deleted at the 5' end of the promoter region and/or at the 3' end of the promoter region, or within the promoter sequence and/or nucleotide substitutions may be introduced. These constructs are then again introduced into cells and their activity and/or functionality are determined.

Instead of measuring the activity of a reporter enzyme, the transcriptional promoter activity (and functionality) can also be determined by measuring the level of RNA that is produced. This level of RNA, such as mRNA, can be measured either at a single time point or at multiple time points and as such the fold increase can be average fold increase or an extrapolated value derived from experimentally measured values. As it is a comparison of levels, any method that measures mRNA levels can be used. In an example, the tissue or organs compared are a seed or seed tissue such as fibers with a leaf or leaf tissue. In another example, multiple tissues or organs are compared. One example for multiple comparisons is fiber cells compared with 2, 3, 4, or more tissues or organs selected from the group consisting of floral tissue, floral apex, pollen, leaf, embryo, shoot, leaf primordia, shoot apex, root, root tip, vascular tissue and cotyledon. As used herein, examples of plant organs are seed, leaf, root, etc. and examples of tissues are leaf primordia, shoot apex, vascular tissue, etc. The activity or strength of a promoter may be measured in terms of the amount of mRNA or protein accumulation it specifically produces, relative to the total amount of mRNA or protein. The promoter expresses an operably linked nucleic acid sequence for example at a level greater than about 0.1%, about 0.2%, greater than about 0.5, 0.6, 0.7, 0.8, or about 0.9%, greater than about 1%, 2%, 3%, 4%, 5%, 6%, 7%, 8%, or about 9%, or greater than about 10% of the total mRNA of the cell it is contained in. Alternatively, the activity or strength of a promoter may be expressed relative to a well-characterized promoter for which transcriptional activity was previously assessed.

As used herein, the term "percent sequence identity" refers to the percentage of identical nucleotides between two segments of a window of optimally aligned DNA. Optimal alignment of sequences for aligning a comparison window are well-known to those skilled in the art and may be conducted by tools such as the local homology algorithm of Smith and Waterman (Waterman, M. S., Chapman & Hall. London, 1995), the homology alignment algorithm of Needleman and Wunsch (1970), the search for similarity method of Pearson and Lipman (1988), and preferably by computerized implementations of these algorithms such as GAP, BESTFIT, FASTA, and TFASTA available as part of the GCG (Registered Trade Mark), Wisconsin Package (Registered Trade Mark from Accelrys Inc., San Diego, Calif.). An "identity fraction" for aligned segments of a test sequence and a reference sequence is the number of identical components that are shared by the two aligned sequences divided by the total number of components in the reference sequence segment, i.e., the entire reference sequence or a smaller defined part of the reference sequence. Percent sequence identity is represented as the identity fraction times 100. The comparison of one or more DNA sequences may be to a full-length DNA sequence or a portion thereof, or to a longer DNA sequence.

The fiber selective promoters or promoter regions as herein described may be used to express coding regions of interest in a cotton plant in a fiber selective manner. To this end, the cotton plant cell may be provided with a transgene comprising the following operably linked DNA regions: (a) a promoter or promoter region as herein described; (b) a DNA encoding a biologically active RNA molecule; and optionally a transcription termination region or a transcription termination and polyadenylation region, preferably functional in a plant cell such as a cotton plant cell.

As used herein "a biologically active RNA" may be further translated into a polypeptide or may the RNA may exert a biological activity itself, as exemplified by inhibitory RNA molecules which decrease the levels of mRNAs of their target proteins available for translation into said target protein. This can be achieved through well-established techniques including co-suppression (sense RNA suppression), antisense RNA, double-stranded RNA (dsRNA), siRNA or microRNA (miRNA). Other exemplary biologically active RNA molecules may be ribozymes catalyzing either their own cleavage or the cleavage of other RNAs. DNA encoding a biologically active RNA may also be referred to as "coding region".

The term "heterologous" refers to the relationship between two or more nucleic acid or protein sequences that are derived from different sources. For example, a promoter is heterologous with respect to an operably linked nucleic acid sequence, such as a coding sequence, if such a combination is not normally found in nature. In addition, a particular sequence may be "heterologous" with respect to a cell or organism into which it is inserted (i.e. does not naturally occur in that particular cell or organism). For example, the chimeric gene disclosed herein is a heterologous nucleic acid.

The present invention is also directed to transgenic cotton plant cells and transgenic cotton plants which comprise a nucleic acid sequence as described above, i.e. a promoter, promoter region or recombinant gene as disclosed herein, operably linked to nucleic acid sequence, including a heterologous nucleic acid sequence, such as a DNA region encoding an expression product of interest.

A transgenic plant cell or plant may be produced by introducing the nucleic acid sequence(s) as described above into plants or plant cells. "Introducing" in connection with the present application relates to the placing of genetic information in a plant cell or plant by artificial means. This can be effected by any method known in the art for introducing RNA or DNA into plant cells, protoplasts, calli, roots, tubers, seeds, stems, leaves, seedlings, embryos, pollen and microspores, other plant tissues, or whole plants. More particularly, "introducing" includes stably integrating into the plant's genome.

A number of methods are available to introduce DNA into cotton plant cells or plants, either by transformation or introgression. Agrobacterium-mediated transformation of cotton has been described e.g. in U.S. Pat. No. 5,004,863, in U.S. Pat. No. 6,483,013 and WO 2000/71733.

Plants may also be transformed by particle bombardment: Particles of gold or tungsten are coated with DNA and then shot into young plant cells or plant embryos. This method also allows transformation of plant plastids. Cotton transformation by particle bombardment is reported e.g. in WO 92/15675.

Further transformation and introgression protocols can also be found in U.S. Pat. No. 7,172,881.

"Introgressing" means the integration of a gene in a plant's genome by natural means, i.e. by crossing a plant comprising the chimeric gene described herein with a plant not comprising said chimeric gene. The offspring can be selected for those comprising the chimeric gene.

Plants containing at least one transformed nucleic acid sequence are referred to as "transgenic plants". Transgenic and recombinant refer to a host organism such as a plant into which a heterologous nucleic acid molecule (e.g. the nucleic acid sequence, the chimeric gene or the vector as described herein) has been introduced. The nucleic acid can be stably integrated into the genome of the plant. Specific methods for introduction are described in connection with the methods disclosed herein.

The plant cell may be a cotton plant cell.

"Cotton" or "cotton plant" as used herein can be any species from the genus *Gossypium* useful for growing harvesting cotton fibers. The most commonly used cotton species are *Gossypium barbadense, G. hirsutum, G. arboreum* and *G. herbaceum*. Further species include *G. africanum* and *G. raimondii*. Also included are progeny from crosses of any of the above species with other species or crosses between such species.

Cotton plants include but are not limited to the following varieties: Coker 312, Coker310, GSC25110, FIBERMAX 819, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 ORO BLANCO PIMA, FIBERMAX FM5013, FIBERMAX FM5015, FIBERMAX FM5017, FIBERMAX FM989, FIBERMAX FM958, FIBERMAX FM832, FIBERMAX FM991, FIBERMAX FM819, FIBERMAX FM800, FIBERMAX FM960, FIBERMAX FM966, FIBERMAX FM981, FIBERMAX FM5035, FIBERMAX FM5044, FIBERMAX FM5045, FIBERMAX FM5013, FIBERMAX FM5015, FIBERMAX FM5017 or FIBERMAX FM5024 and plants with genotypes derived thereof.

A cotton plant cell may be any cell comprising essentially the genetic information necessary to define a cotton plant, which may, apart from the chimeric gene disclosed herein, be supplemented by one or more further transgenes. Cells may be derived from the various organs and/or tissues forming a cotton plant, including but not limited to fruits, seeds, embryos, reproductive tissue, meristematic regions, callus tissue, leaves, roots, shoots, flowers, vascular tissue, gametophytes, sporophytes, pollen, and microspores.

The present application also discloses a transgenic plant consisting of the transgenic cotton plant cells described hereinabove, or comprising the chimeric gene or the vector described herein stably integrated in the plant genome. This may be effected by transformation protocols described elsewhere in this application.

In another embodiment, the present invention relates to a seed generated from a transgenic plant described herein, wherein said seed comprises the chimeric gene described herein.

Seed is formed by an embryonic plant enclosed together with stored nutrients by a seed coat. It is the product of the ripened ovule of gymnosperm and angiosperm plants, to the latter of which cotton belongs, which occurs after fertilization and to a certain extent growth within the mother plant.

Further disclosed herein are cotton fibers and cotton seed oil obtainable or obtained from the plants disclosed herein. Cotton fibers disclosed herein can be distinguished from other fibers by applying the detection method disclosed in WO2010/015423 and checking for the presence of the recombinant promoter or the chimeric genes as herein described in the fibers. Accordingly, the nucleic acid of at least part of the promoter regions herein described may also be used for tracking cell walls, in particular cotton fibers according to the invention.

Also disclosed herein are yarns and textiles made from the fibers disclosed herein as well as foodstuff and feed comprising or made of the cotton seed oil disclosed herein. A method to obtain cotton seed oil comprising harvesting cotton seeds from the cotton plant disclosed herein and extracting said oil from said seeds is also disclosed. Further, a method to produce cotton fibers comprising growing the cotton plant disclosed herein and harvesting cotton from said cotton plants is also disclosed.

The cotton plants or seed comprising the chimeric gene disclosed herein or obtained by the methods disclosed herein may further be treated with cotton herbicides such as Diuron, Fluometuron, MSMA, Oxyfluorfen, Prometryn, Trifluralin, Carfentrazone, Clethodim, Fluazifop-butyl, Glyphosate, Norturazon, Pendimethalin, Pyrithiobac-sodium, Trifloxysulfuron, Tepraloxydim, Glufosinate, Flumioxazin, Thidiazuron; cotton insecticides such as Acephate, Aldicarb, Chlorpyrifos, Cypermethrin, Deltamethrin, Abamectin, Acetamiprid, Emamectin Benzoate, Imidacloprid, lndoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chloropyridin-3-yl) methyl](2,2-difluorethyl)amino]furan-2(5H)-on, Thiodicarb, Avermectin, Flonicamid, Pyridalyl, Spiromesifen, Sulfoxaflor; and cotton fungicides such as Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin. For a treatment with cotton herbicides, said cotton plants or seed preferably further comprise a trait conferring a respective herbicide tolerance or are naturally tolerant to a herbicide.

The following non-limiting Examples describe the construction of a recombinant fiber-selective promoter, and the construction of chimeric genes for selective expression in developing fiber cells. Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK.

Throughout the description and Examples, reference is made to the following sequences represented in the sequence listing:

SEQ ID No 1: nucleotide sequence of the recombinant promoter region FB8-like2_FSR.

SEQ ID No 2: nucleotide sequence of the fiber selective promoter region of an FB8-like2 gene from *Gossypium hirsutum* (also described in EP13189991).

SEQ ID No 3: nucleotide sequence of the FSR region from the promoter of the cotton gene encoding the cotton lipid transfer protein Fsltp4.

SEQ ID No 4: nucleotide sequence of the core FSR region from the promoter of the cotton gene encoding the cotton lipid transfer protein Fsltp4.

SEQ ID No 5: nucleotide sequence of the fiber selective promoter region of an FB8-like1 gene from *Gossypium hirsutum* (also described in US2013/0081154).

SEQ ID No 6: nucleotide sequence of the promoter region of the Fblate gene from *Gossypium hirsutum* (4-4 promoter region; also described in U.S. Pat. No. 6,211,430).

SEQ ID No 7: nucleotide sequence of the promoter region of the Fblate2 gene from *Gossypium hirsutum* (also described in WO96/40924).

SEQ ID No 8: nucleotide sequence of the T-DNA of vector pTDBI263.

EXAMPLES

Example 1: Construction of a Recombinant FB8like2_FSR Promoter Region

The recombinant FB8like2_FSR promoter region was constructed by inserting the fiber-specificity region (FSR) and some flanking sequences from the cotton FSltp4 promoter (Delaney et al. 2007, Plant Cell Physiol. 48(10): 1426-1437) into the Fb8-like-2 promoter between positions 426 and 427. This FSR suppresses activity of the promoter outside cotton fiber cells.

The sequence of the chimeric promoter below is provided in FIG. 1 (the sequence in normal font originates from Fb8-like-2, the nucleotide sequence in bold originates from Fsltp4 promoter, including the FSR, indicated in bold, italics, underlined font).

The site of insertion of the FSR was chosen such that the distance between the FSR and the transcription start site was similar within the recombinant promoter to that within the Fsltp4 promoter and at a point where the related Fb8-like-1 promoter (and the 4-4 and Fblate2 promoters) had an insertion as well (see alignment in FIG. 3). In this way the chance that both the FSR and the promoter are still functional was maximized.

The recombinant promoter region thus comprises:

a. position 1 to position 426: nucleotide sequence of FB8like2 promoter region (SEQ ID No. 2) from position 1 to 426 b. position 427 to position 557: nucleotide sequence of SEQ ID No. 3 (including FSR region)

c. position 558 to position 1090: nucleotide sequence of FB8like2 promoter region (SEQ ID No. 2) from position 427 to 959.

Example 2: Expression of Chitin Synthase and Gfa Under Control of the FB8like2_FSR Promoter Region in Cotton Chitin synthases can be expressed in cotton plants to increase positive charges in the cotton fiber by introducing chitin polymers into the fiber cell wall. For this, fiber-preferential or fiber-specific expression is important since plants transformed with a chitin synthase gene mostly do not show an appreciable phenotype if the promoter controlling expression of the chitin synthase is driving expression in many other tissues or cell types than fiber cells.

The following T-DNA vector comprising chimeric genes according to the invention was generated: T-DNA vector (pTDBI263) comprising a nucleic acid sequence encoding the *Neurospora crassa* chitin synthase 2 gene comprising a Golgi-targeting signal from Arabidopsis thaliana under control of the recombinant FB8like2_FSR promoter region and further comprising a recombinant epsps gene as selectable marker gene, as well as a recombinant gene comprising the gfa (glutamine:fructose-6-phosphate amidotransferase) coding region from *E. coli* (Frohberg and Essigmann, 2006) under control of the FB8like2_FSR promoter region. The nucleotide sequence of the T-DNA of this vector is represented in SEQ ID No. 8. The genetic elements of the vector are indicated in the features of SEQ ID No. 8.

This vector was transferred into an appropriate Agrobacterium strain which was used for transforming cotton variety Coker312-17. The transformation frequencies were determined and compared to transformation experiments with similar vectors but wherein the chitin synthase and gfa are under control of other fiber-selective promoters. Also included was a control T-DNA vector which did not comprise the "deleterious" coding regions. The results are summarized in Table 1.

TABLE 1

Transformation efficiency and percentage of fertile plants obtained.

| Experiment | Construct | Promoter(s) (chs/gfa) | Transformation Efficiency (%) | % Fertility |
|---|---|---|---|---|
| EXPERIMENT 1 | pTIB358 | Fb8-like-1/Fb8-like-1 | 7.0 | 38 |
| | pTIB359 | Fb8-like-2/Fb8-like-2 | 7.8 | 28 |
| | pTIB360 | FS18/SCW-PRP | 9.7 | 25 |
| | pTIB361 | SCW-PRP/FS18 | 9.6 | 13 |
| | pTDBI263 | Fb8like2_FSR/Fb8-like2_FSR | 23.8 | 35 |
| | pTIF78 | — | 23.4 | 35 |
| EXPERIMENT 2 | pTIB344 | FS18/FS18 | 7.4 | 20 |
| | pTIB345 | SCW-PRP/SCW-PRP | 9.2 | 14 |
| | pTIB348 | Fb-B6-1/Fb-B6-1 | 0.2 | 0 |
| | pTIB349 | Fb-B6-2/Fb-B6-2 | 0.5 | 40 |
| | pTIB362 | FS18/Fb-B6-1 | 5.4 | 13 |
| | pTIB363 | SCW-PRP/Fb-B6-1 | 6.5 | 23 |
| | pTDBI263 | Fb8like2_FSR/Fb8-like2_FSR | 20.0 | 35 |

As can be deduced from the results summarized in Table 4, T-DNA vectors comprising the recombinant promoter regions of the invention to drive expression of chitin synthase and gfa coding region resulted in significantly higher transformation efficiencies than when using T-DNA vectors with other fiber-selective promoter regions, similar to transformation experiments using a "neutral" T-DNA vector. Also the percentage of fertile plants obtained was similar to those obtained when using a neutral T-DNA vector. It is thought that this increased frequencies are caused by the lesser expression of gfa and chitin synthase outside of the fibers, as such expression outside of fibers causes unwanted phenotypes, and may be deleterious for plant cells other than fiber (initiation) cells.

The invention claimed is:

1. A recombinant DNA molecule comprising a chimeric promoter, which comprises in order:
   (i) a DNA molecule comprising a fiber specificity region of a cotton lipid transfer protein gene promoter comprising a nucleotide sequence having the nucleotide sequence of SEQ ID NO: 4, operably linked to
   (ii) a DNA molecule comprising a nucleotide sequence having about 500 consecutive nucleotides of the 3'end of the FB8-like 2 promoter of SEQ ID NO: 2, and wherein the chimeric promoter has the cotton fiber specific promoter activity of the synthetic promoter as set forth in SEQ ID NO: 1.

2. The recombinant DNA molecule of claim 1, wherein the DNA molecule of part (i) comprising the fiber specificity region is preceded by a DNA molecule comprising a nucleotide sequence of about 400 consecutive nucleotides of the 5'end of the FB8-like 2 promoter of SEQ ID NO: 2.

3. The recombinant DNA molecule of claim 1, wherein the nucleotide sequence of about 500 consecutive nucleotides of the 3' end of the FB8-like 2 promoter of SEQ ID NO: 2 comprises the nucleotide sequence of SEQ ID NO: 2 from the nucleotide at position 427 to the nucleotide at position 922.

4. The recombinant DNA molecule of claim 1, wherein the nucleotide sequence of about 500 consecutive nucleotides of the 3' end of the FB8-like 2 promoter of SEQ ID NO: 2 comprises the nucleotide sequence of SEQ ID NO: 5 from the nucleotide at position 911 to the nucleotide at position 1405.

5. The recombinant DNA molecule of claim 1, wherein the nucleotide sequence of about 500 consecutive nucleotides of the 3' end of the FB8-like 2 promoter of SEQ ID NO: 2 comprises the nucleotide sequence of SEQ ID NO: 6 from the nucleotide at position 3638 to the nucleotide at position 4132.

6. The recombinant DNA molecule of claim 1, wherein the nucleotide sequence of about 500 consecutive nucleotides of the 3' end of the FB8-like 2 promoter of SEQ ID NO: 2 comprises the nucleotide sequence of SEQ ID NO: 7 from the nucleotide at position 1781 to the nucleotide at position 2276.

7. The recombinant DNA molecule of claim 2, wherein the DNA molecule comprising a nucleotide sequence of about 400 consecutive nucleotides of the 5' end of the FB8-like 2 promoter of SEQ ID NO: 2 comprises the nucleotide sequence of SEQ ID NO: 5 from the nucleotide at position 61 to the nucleotide at position 475.

8. The recombinant DNA molecule of claim 2, wherein the DNA molecule comprising a nucleotide sequence of about 400 consecutive nucleotides of the 5' end of the FB8-like 2 promoter of SEQ ID NO: 2 comprises the nucleotide sequence of SEQ ID NO: 6 from the nucleotide at position 2787 to the nucleotide at position 3202.

9. The recombinant DNA molecule of claim 2, wherein the DNA molecule comprising a nucleotide sequence of about 400 consecutive nucleotides of the 5' end of the FB8-like 2 promoter of SEQ ID NO: 2 comprises the nucleotide sequence of SEQ ID NO: 7 from the nucleotide at position 1047 to the nucleotide at position 1464.

10. The recombinant DNA molecule of claim 1, wherein the chimeric promoter comprises a nucleotide sequence having at least 98% nucleotide sequence identity to the nucleotide sequence of SEQ ID NO: 1 [from the nucleotide at position 1 to the nucleotide at position 1053].

11. The recombinant DNA molecule of claim 1, wherein said chimeric promoter has cotton fiber-selective expression of a coding region operably linked thereto.

12. A recombinant nucleic acid construct comprising the following operably linked DNA molecules:
   (a) a recombinant DNA molecule according to claim 1;
   (b) a DNA molecule encoding a biologically active RNA molecule; and
   (c) a DNA molecule encoding a transcription termination region or a transcription termination and polyadenylation region.

13. The recombinant nucleic acid construct of claim 12, wherein said DNA molecule encoding said biologically active RNA molecule codes for a chitin synthase 2 of *Neurospora crassa* or a glutamine:fructose-6-phosphate amidotransferase of *E. coli*.

14. A cotton plant cell transformed with a recombinant nucleic acid construct according to claim 12.

15. A cotton plant transformed with a recombinant nucleic acid construct according to claim 12.

16. A method for making a transgenic cotton plant cell or cotton plant comprising transforming a cell of a cotton plant with a recombinant nucleic acid construct according to claim 12, and regenerating a transformed cotton plant from said transformed cotton plant cell.

17. The method of claim 16 comprising further the step of harvesting fibers from said transformed cotton plant.

18. A fiber obtained from the transformed cotton plant of claim 15, wherein the fiber comprises the recombinant nucleic acid construct.

* * * * *

SEQUENCE LISTING

<160> NUMBER OF SEQ ID NOS: 8

<210> SEQ ID NO 1
<211> LENGTH: 1090
<212> TYPE: DNA
<213> ORGANISM: Artificial Sequence
<220> FEATURE:
<223> OTHER INFORMATION: Recombinant FB8-like2::FSR promoter
<220> FEATURE:
<221> NAME/KEY: misc_feature
<222> LOCATION: (1)..(426)
<223> OTHER INFORMATION: 3' end of FB8-like2 promoter
<220> FEATURE:
<221> NAME/KEY: misc_feature
<222> LOCATION: (427)..(557)
<223> OTHER INFORMATION: FSR region of FSltp4 promoter
<220> FEATURE:
<221> NAME/KEY: misc_feature
<222> LOCATION: (558)..(1090)
<223> OTHER INFORMATION: 5' end of FB8-like2 promoter

<400> SEQUENCE: 1

```
aagcttaaaa tcacttatca atttcaaaaa cagaggttag ccgaatgcta agagcttaaa      60
aatggcttct tttgtttctt tttcttgcaa acggtggaga gaagagggaa atgaagattg     120
accatatctt tttttattat gttttaacat ataatattaa taatttaatc ataattatac     180
tttggtgaat gtgacagtgg ggatatacgt aaagtatata acattatact ttttgcaagc     240
agttggctgg tctacccaag agtgatcaaa ttttgagctg ccttcaatga gccaattttt     300
gcctataatg gataaaggca ctttgtctag ttcaactgct cacagaataa tgttaaaatg     360
aaattaaaac aaggtgggct ggtcacacca aaaaataaa  atattaatgt ggtgtttggt     420
tagtcgattt tatattagtt ccatggcata ccgcctggaa aaggaaaatt catgtaaata     480
atatatttat aaaaatttat attaaaacta aatgaaattt tagttgaaat agttaagtta     540
aaaagagtaa aatttataat ttatcataat tttatagaaa ttgagactaa aaaacattaa     600
gagaataaat tctataacaa agacaattta gtaaaaatgt cctttaggt  aattttaagt     660
actcttaacc aaaataaaaa attcaaatca aattaaccaa ataagataat ataacatacg     720
gaacatccca cttataatct tacatccccg taatcttatt atgaaaagta atcttatatt     780
actcgaatca aatgctctca caaactatta tctaaataaa gaaaaacact taatttttat     840
aacatttttt ttcatatatt tgaaagatta tattttgtat ttttacgtaa aaatatttga     900
catagattga gcacctttt  aacataattc caccataagt caattatgta gatgagaaat     960
tggtacaaac aacgtggagc caaatcccac caaaccatct ctcatcctct cctataaaag    1020
gcttgctaca catagacaac aatccacaca aaaatacact taaaattctt ttctttctat    1080
ttggttaacc                                                           1090
```

<210> SEQ ID NO 2
<211> LENGTH: 959
<212> TYPE: DNA
<213> ORGANISM: Gossypium hirsutum

<400> SEQUENCE: 2

```
aagcttaaaa tcacttatca atttcaaaaa cagaggttag ccgaatgcta agagcttaaa      60
aatggcttct tttgtttctt tttcttgcaa acggtggaga gaagagggaa atgaagattg     120
accatatctt tttttattat gttttaacat ataatattaa taatttaatc ataattatac     180
tttggtgaat gtgacagtgg ggatatacgt aaagtatata acattatact ttttgcaagc     240
agttggctgg tctacccaag agtgatcaaa ttttgagctg ccttcaatga gccaattttt     300
```

```
gcctataatg gataaaggca ctttgtctag ttcaactgct cacagaataa tgttaaaatg      360
aaattaaaac aaggtgggct ggtcacacca aaaaaataaa atattaatgt ggtgtttggt      420
tagtcgaatt tatcataatt ttatagaaat tgagactaaa aaacattaag agaataaatt      480
ctataacaaa gacaatttag taaaaatgtc cttttaggta attttaagta ctcttaacca      540
aaataaaaaa ttcaaatcaa attaaccaaa taagataata taacatacgg aacatcccac      600
ttataatctt acatccccgt aatcttatta tgaaagtaa tcttatatta ctcgaatcaa       660
atgctctcac aaactattat ctaataaag aaaaacactt aatttttata acattttttt       720
tcatatattt gaaagattat attttgtatt tttacgtaaa aatatttgac atagattgag      780
caccttttta acataattcc accataagtc aattatgtag atgagaaatt ggtacaaaca      840
acgtggagcc aaatcccacc aaaccatctc tcatcctctc ctataaaagg cttgctacac      900
atagacaaca atccacacaa aaatacactt aaaattcttt tctttctatt tggttaacc      959
```

```
<210> SEQ ID NO 3
<211> LENGTH: 131
<212> TYPE: DNA
<213> ORGANISM: Gossypium hirsutum
<220> FEATURE:
<221> NAME/KEY: misc_feature
<222> LOCATION: (11)..(94)
<223> OTHER INFORMATION: FSR core region from promoter FSltp4

<400> SEQUENCE: 3
attttatatt agttccatgg cataccgcct ggaaaaggaa aattcatgta ataatatat       60 ttataaaaat ttatattaaa actaaatgaa attttagttg aaatagttaa gttaaaaga      120 gtaaaattta t                                                          131
```

```
<210> SEQ ID NO 4
<211> LENGTH: 84
<212> TYPE: DNA
<213> ORGANISM: Gossypium hirsutum

<400> SEQUENCE: 4
agttccatgg cataccgcct ggaaaaggaa aattcatgta ataatatat ttataaaaat       60 ttatattaaa actaaatgaa attt                                            84
```

```
<210> SEQ ID NO 5
<211> LENGTH: 1437
<212> TYPE: DNA
<213> ORGANISM: Gossypium hirsutum

<400> SEQUENCE: 5
catgattagt tagatcaagc ttttgagtct tcaaaaacat aaaaattaca aaaaaaaac       60 aaacttaaaa tcatttatca atttgaacaa caaagcttgg ccgaatgcta agagcttaaa    120
aatggcttct tttgtttctt tttgttgcaa acggtggaga gaagagggaa atgaagattg    180
accatatttt tttattatgt tttaacatat aatattaata atttaatcat aattatactt    240
tggtgaatgt gacagtgggg agatacgtaa agtatataac attatacttt ttgcaagcag    300
ttggctggtc tacccaagag tgatcaaagt ttgagctgcc ttcaatgagc caattttgc     360 ccataatgga taaaggcaat ttgtttagtt caactgctca cagaataatg ttaaaatgaa    420
attaaaataa ggtggcctgg tcacacacac aaaaaaaaac taatgttggt tggttgaatt    480
ttatattacg gaatgtaata ttatatttta aaataaaatt atgttattta gattcttaat    540
```

| | |
|---|---:|
| attttgagca ttccatacta taatttcgta tacataatat taaaatatag taatataaag | 600 |
| tgtaattaac tttaaattac aagcataata ttaaattttg aatcaattaa ttttatttc | 660 |
| tattatttta attaatttag tctattttt caaaataaaa tttaaatcta aataaaaata | 720 |
| attttccctt aatgttgaaa caactcatgt tatacttcaa aattataagt attatattta | 780 |
| ccttgatgat ttatttatta gtatattaat tctgattata attatggtgg gatacaatcg | 840 |
| ctttccacta aatattttaa ctatgattta taaatttatt tcaacatcgt atatttactt | 900 |
| attaatacat aatttatcat aatttatgg aaattgagac caagaaacat taagagaaca | 960 |
| aattctataa caaagacaat ttagaaaaaa atgtactttt aggtaatttt aagtactctt | 1020 |
| aaccaaacac aaaaattcaa atcaaatgaa ctaaataaga taatataaca tacggaacat | 1080 |
| cttacttgta atcttacatt cccataattt tattatgaaa aataatctta tattactcga | 1140 |
| actaaatgtt gtcacaaatt attatctaaa taaagaaaaa cacttaattt ttataacatt | 1200 |
| ttttcatata tttgaaagat tatattttgt atatttacgt aaaaatattt gacatagatt | 1260 |
| gagcaccttc ttaacataat cccaccataa gtcaagtatg tagatgagaa attggtacaa | 1320 |
| acaacgtggg gccaaatccc accaaaccat ctctcattct ctcctataaa aggcttgcta | 1380 |
| cacatagaca acaatccaca cacaaataca cgttcttttc tttctatttg attaacc | 1437 |

<210> SEQ ID NO 6
<211> LENGTH: 4167
<212> TYPE: DNA
<213> ORGANISM: Gossypium hirsutum

<400> SEQUENCE: 6

| | |
|---|---:|
| actaaaggga acaaaagctg gagctccacc gcggtggcgg ccgctctaga actagtggat | 60 |
| cccccgtgga ctaaacaaaa catgggaaga tttgctgtaa aaaaataaaa gaagcttact | 120 |
| caataacact ttgtgaattg tatacaaaag actcaatgaa aaacaataac tcaatacact | 180 |
| ttttttcact gatttacatc ctttatatag gctgaaacta caacaacttt agctaaaaaa | 240 |
| ataggataac ctaatagcaa atcacaatc agatattaaa ccatgatttt agctaaccat | 300 |
| ttaacaactt tattgaaact aatttgaata tttcatctgc tgatatgccc aagattttag | 360 |
| gccactaacc gatttggtgg tgaacttaa catgtcatgc atttgtaact gtttgaaaca | 420 |
| agttttttgc attattttac tatatgaact gtttgattag gttgagttac acactgagct | 480 |
| tgtaagctca ctcaaatttt tctaatttct aaggtgatca gcaaacttag gaccgggcgg | 540 |
| cgtacgagag ctcggattga ttttctagtt aataaataag acgatttatg ttttaaact | 600 |
| attatggact ttttggacta tgtaactgtt tgggactta tttttgtttt ttatttgctt | 660 |
| ttttggatt tagtaattat tattttaaa ctgcaaaatt atatgttttt acaaactaag | 720 |
| tcacagtttt caaaattcca taacttagaa ttttcgctg caaataaag taatcattta | 780 |
| agtgtttttt ctgtaataaa ataaataaat aattttaacg agtatttcc taaaaattgg | 840 |
| aaattgattt accaaaatta gtatgtcaaa acacatgttt atatgttaca gggcgatatc | 900 |
| gtctaggcaa ataacatcta ggcgggttt ggagtgttac agggcgagtg ggctcatttt | 960 |
| gagtaagtat agttagggcc gagtttaga ttgcatattc aaggtcaaag attttgtaaa | 1020 |
| cttcgatgaa tgatatgtat gattgtccga ttaacgaaat atgttttttt cttttgtgtg | 1080 |
| tgttttatct cgtgtgataa gtatatagta tgttttattc caattcttat ggcatgtgac | 1140 |
| attgtggcta ttctaattaa attgatttgt tattattgaa atctgatgca tctgttctac | 1200 |
| aaagcatgga atctcatgcc tactgctttc tgttaaagat acgattgcaa gtttaacatg | 1260 |

```
cttactatttt tgattttgtc cttgcatgct atgtcacatt acatggggtt gggatgatat    1320
ggtaaggagg aagttttgac agtttaatga tttgcactat ctggtggttt aaccacatat    1380
ttgttatggc atcttgactg cggttatggt ggctcgaccg cccatatctg ttctggaaat    1440
ttatctgtga ctctggtggc attgtctaca attatttgtt ggtgtgtttt ggatggacga    1500
gtcgtgggga actctatttg gtgtgttgcg gagttgggta ggaaattttc gaaaaaaatt    1560
tgcattgtgt ttttctgaaa aatattgcat taacataatc atgcattctc aattttggtc    1620
aattgaacgt tataaaattc tctatgatat cctgatctgt ttattacatt atatgtgttt    1680
atgcttgagt taagtcaaac attgagattc atagctcacc caattattta atcatttcag    1740
gcaatctgca gacttaggat tggatggcgt tcaggagctt ggattggttt tctcacatca    1800
tattttatta ataattatt aattaaaatt tatggactgtct ggactgtct gactaatttt    1860 cagaatttta ttttggtttt gggttttgtt gaattttta gataattatt ttaaatattc    1920
tgcataattt ttctgttatt tgaaaaggat gttcgaattt tttttcaaaa ttgaaacgtt    1980 taagaattt tactactgca aattcagaat aagtgaattt gttttttaga aagattaaat    2040
aagttagtat tacgatttt agtttgattt ggtggaaagt aatgtatgtt tttgaacata    2100
attatttgac aataattaag ttttctaggg aataaacgga aatatcttct tcttttttgt    2160
aaaattacta atgcaagaac aaacaacgtt tggggagca aataatctag ctttaagtag    2220
tcagtgtaac tctcaaaatc tggtcataac ttctaggctg agtttgctgt gctacagtag    2280
taagtctata gaaacttacc tgacaaaacg acatgacgtc agggtcgaat ctacaacttt    2340
tcctttttct tcaattaaca tatggttgat tcaagttccg atctataata atttattacg    2400
atttatcaat ttcaattacc ttatatcatc ctattataaa tataagtcag ttcaattcag    2460
ttttcgaaag ttcccaaaaa ttttgaattt tattaaattt attccctaaa accgaaatag    2520
ttatatcttt caaatttaag tttcattttt caatccgatt tcaatttcat ccttttataa    2580
ctctctatta tctataatta cataaatttc aaattaattt tgaaatattt acactttagt    2640
ccctaagttc aaaactataa attttcactt tagaaattaa tcattttttca catctaagca    2700 tcaaatttaa ccaaatgaca caaatttcat gattagttag atcaagcttt tgagtcttca    2760
aaacataaaa attacaaaaa aaaaacaaac ttaaaatcat ttatcaattt gaacaacaaa    2820
gcttggccga atgctaagag cttaaaaatg gcttcttttg tttcttttg ttgcaaacgg    2880 tggagagaag agggaaatga agattgacca tatttttta ttatgttta acatataata    2940 ttaataattt aatcataatt atactttggt gaatgtgaca gtggggagat acgtaaagta    3000
ttttaacatt atacttttg caagcagttg gctggtctac ccaagagtga tcaaagtttg    3060
agctgccttc aatgagccaa ttttgcccca taatggataa aggcaatttg tttagttcaa    3120
ctgctcacag aataatgtta aaatgaaatt aaaataaggt ggcctggtca cacacacaaa    3180
aaaaaactaa tgttggttgg ttgaatttta tattacggaa tgtaatatta tatttaaaa    3240 taaaattatg ttatttagat tcttaatatt ttggagcatt ccatactata atttcgtaac    3300
ataatattaa aatatagtaa tataaagtgt aattaacttt aaattacaag cataatatta    3360
aattttgaat caattaattt ttatttctat tatttttaatt aatttagtct atttttttcaa    3420 aataaaattt aaatctaaat aaaaataatt tttccttaat gttgaaacaa ctcatgttat    3480
acttcaaaat tataagtatt atatttaccct tgatgattta tttattagta tattaattct    3540
gattataatt atggtgggat acaatcgctt tccactaaat attttaacta tgatttataa    3600
```

| | |
|---|---|
| atttatttca acatcgtata tttacttatt aatacataat ttatcataat tttatggaaa | 3660 |
| ttgagaccaa gaaacattaa gagaacaaat tctataacaa agacaattta gaaaaaaatg | 3720 |
| tacttttagg taattttaag tactcttaac caaacacaaa aattcaaatc aaatgaacta | 3780 |
| aataagataa tataacatac ggaacatctt acttgtaatc ttacattccc ataatttat | 3840 |
| tatgaaaaat aatcttatat tactcgaact aaatgttgtc acaaattatt atctaaataa | 3900 |
| agaaaaacac ttaatttta taacattttt tcatatattt gaaagattat attttgtata | 3960 |
| tttacgtaaa aatatttgac atagattgag caccttctta acataatccc accataagtc | 4020 |
| aagtatgtag atgagaaatt ggtacaaaca acgtggggcc aaatcccacc aaaccatctc | 4080 |
| tcattctctc ctataaaagg cttgctacac atagacaaca atccacacac aaatacacgt | 4140 |
| tctttctttt ctatttgatt aaccatg | 4167 |

<210> SEQ ID NO 7
<211> LENGTH: 2317
<212> TYPE: DNA
<213> ORGANISM: Gossypium hirsutum

<400> SEQUENCE: 7

| | |
|---|---|
| ctgcagactt aggattggat ggcgttcagg agcttggatt ggttttctca catcatattt | 60 |
| tattaaataa ttattaatta aaatttatgg acttttggac tgtctgacta attttcagaa | 120 |
| ttttattttg gttttgggtt tgttgagtt ttttagataa ttatttaaa tattctgcat | 180 |
| aattttctg ttatttgaaa aggatgttcg aattttttt caaaattgaa acgtttaaga | 240 |
| attttacta ctgcaaattc agaataagtg aatttgtttt ttagaaagat taaataagtt | 300 |
| agtattacga ttttagttt gatttggtgg aaagtaatgt atgtttttga acataattat | 360 |
| ttgacaataa ttaagttttc taggaaataa acggaaatat cttcttttt ttttgtaaaa | 420 |
| ttactaatgc aagaacaaac aacgttttgg gaagcaaata atctagcttt aagtagtcag | 480 |
| tgtaactctc aaaatctggt cataacttct aggctgagtt tgctgtgcta cagtagtaag | 540 |
| tctatagaaa cttacctgac aaaacgacat gacgtcaggg tcgaatctac aacttttcct | 600 |
| ttttcttcaa ttaacatatg gttgattcaa gttccgatct ataataattt attacgattt | 660 |
| atcaatttca attaccttat atcatcctat tataaatata agtcagttca attcagtttt | 720 |
| cgaaagttcc ctaaaatttt gaatttttatt aaatttattc cctaaaaccg aaatagtgat | 780 |
| atctttcaaa tttaagtttc attttcaat ccgatttcaa tttcatcctt ttataactct | 840 |
| ctatgatcta taattacata aatttcaaac taattttgaa atatatacac tttagtccct | 900 |
| aagttcaaaa ctataaattt tcactttaga aattaatcat ttttcacatc taagcatcaa | 960 |
| atttaaccaa atgacacaaa tttcatgatt agttagatca agcttttgag tcttcaaaaa | 1020 |
| cataaaaatt acaaaaaaaa aaaaacaaac ttaaaatcat ttatcaattt gaacaacaaa | 1080 |
| gcttggccga atgctaagag cttaaaaatg gcttcttttg tttctttttg ttgcaaacgg | 1140 |
| tggagagaag agggaaatga agattgacca tattttttta ttatgttta acatataata | 1200 |
| ttaataattt aatcataatt atactttggt gaatgtgaca gtggggagat acgtaaagta | 1260 |
| tataacatta tacttttgc aagcagttgg ctggtctatc caagagtgat caaagtttga | 1320 |
| gctgccttca atgagccaat ttttgcccat aatggataaa ggcaatttgt ttagttcaac | 1380 |
| tgctcacaga ataatgttaa aatgaaatta aaataaggtg gcctggtcac acacacacaa | 1440 |
| aaaaaaaact aatgttggtt ggttgaattt tatattacgg aatgtaatgt tatatttaa | 1500 |
| aataaaatta tgttatttag attcttaata ttttgagcat tccatactat aatctcgtat | 1560 |

```
acataatatt aaaatatagt aatataaagt gtaattaact ttaaattaca agcataatat    1620
taaattttga atcaattaat ttttatttct attattttaa ttaatttagt ctatttttc     1680 aaaataaaat ttaaatctaa ataaaaataa tttttcctta atattattaa taaatttatt    1740
tcaacatcat atatttactt attaatacat aaattataat aatttatcat aattttatgg    1800
aaattgagac caagaaacat taagagaaca aattctataa caaagacaat ttagtaaaaa    1860 tgtacttta ggtaatttta agtactctta accaaacaca aaaattcaaa tcaaatgaac     1920
caaataagat aatataacat acagaatatc ctacttgtat tcttacattc ccgtaatcat    1980
attatgaaaa gtaatattat attacctgag ccaaatgctc tcacaaacta ttatccaaaa    2040
aaaaaatgtt gaatataatt tttataacat tttttcatat atttgcaaga ttatattttg    2100
tatatttacg taaaaatatt tgacatagat tgaacacctt cttaacataa tcccaccata    2160
agtcaagtat gtagatgaga aattggtaca aacaacgtgg ggccaaatcc caccaaacca    2220
tctctcatcc tctcctataa aaggctagtt acacatacac aacaatccac acacaaatac    2280
actcaaaatt ctttgctttg tatttcggtt aaccatg                            2317
```

```
<210> SEQ ID NO 8
<211> LENGTH: 11990
<212> TYPE: DNA
<213> ORGANISM: Artificial Sequence
<220> FEATURE:
<223> OTHER INFORMATION: T-DNA of vector pTDBI623
<220> FEATURE:
<221> NAME/KEY: misc_feature
<222> LOCATION: (1)..(25)
<223> OTHER INFORMATION: Right border repeat from the T-DNA of
      Agrobacterium tumefaciens
<220> FEATURE:
<221> NAME/KEY: misc_feature
<222> LOCATION: (61)..(1150)
<223> OTHER INFORMATION: Chimeric promoter region FB8-like2-FSR
<220> FEATURE:
<221> NAME/KEY: misc_feature
<222> LOCATION: (1151)..(1255)
<223> OTHER INFORMATION: coding sequence for the Golgi retention peptide
      of the beta-1,2-xylosyltransferase gene of Arabidopisis thaliana
<220> FEATURE:
<221> NAME/KEY: misc_feature
<222> LOCATION: (1256)..(4087)
<223> OTHER INFORMATION: coding sequence for the chtin synthase 2 gene
      of Neurospora crassa
<220> FEATURE:
<221> NAME/KEY: misc_feature
<222> LOCATION: (4099)..(4323)
<223> OTHER INFORMATION: sequence including the 3' untranslated region
      of the 35S transcript of CaMV
<220> FEATURE:
<221> NAME/KEY: misc_feature
<222> LOCATION: (4800)..(4930)
<223> OTHER INFORMATION: chimeric promoter FB8-like2_FSR
<220> FEATURE:
<221> NAME/KEY: misc_feature
<222> LOCATION: (5464)..(7293)
<223> OTHER INFORMATION: coding region of the glutamine:fructose-6-
      phosphate amidotransferase gene of E. coli adapted to plant codon
      usage
<220> FEATURE:
<221> NAME/KEY: misc_feature
<222> LOCATION: (7311)..(7971)
<223> OTHER INFORMATION: 3' untranslated sequence of Arabidopsis
      thaliana histone H4 gene
<220> FEATURE:
<221> NAME/KEY: misc_feature
<222> LOCATION: (8021)..(8937)
<223> OTHER INFORMATION: plant- expressible mutant epsps gene
<220> FEATURE:
<221> NAME/KEY: misc_feature
```

```
<222> LOCATION: (11962)..(11986)
<223> OTHER INFORMATION: LB: Left border repeat of the T-DNA of
      Agrobacterium tumefaciens

<400> SEQUENCE: 8
aattacaacg gtatatatcc tgccagtact gggcccctc gagggcgatc gcgcggccgc      60
aagcttaaaa tcacttatca atttcaaaaa cagaggttag ccgaatgcta agagcttaaa    120
aatggcttct tttgtttctt tttcttgcaa acggtggaga gaagagggaa atgaagattg    180
accatatctt tttttattat gttttaacat ataatattaa taatttaatc ataattatac    240
tttggtgaat gtgacagtgg ggatatacgt aaagtatata acattatact ttttgcaagc    300
agttggctgg tctacccaag agtgatcaaa ttttgagctg ccttcaatga gccaattttt    360
gcctataatg gataaaggca cttttgtctag ttcaactgct cacagaataa tgttaaaatg   420
aaattaaaac aaggtgggct ggtcacacca aaaaaataaa atattaatgt ggtgtttggt    480
tagtcgattt tatattagtt ccatggcata ccgcctggaa aaggaaaatt catgtaaata    540
atatatttat aaaaatttat attaaaacta atgaaatttt tagttgaaat agttaagtta   600
aaaagagtaa aatttataat ttatcataat tttatagaaa ttgagactaa aaaacattaa    660
gagaataaat tctataacaa agacaattta gtaaaaatgt ccttttaggt aattttaagt    720
actcttaacc aaaataaaaa attcaaatca aattaaccaa ataagataat ataacatacg    780
gaacatccca cttataatct tacatcccg taatcttatt atgaaaagta atcttatatt    840
actcgaatca aatgctctca caaactatta tctaaataaa gaaaaacact taattttttat  900
aacatttttt ttcatatatt tgaaagatta tattttgtat ttttacgtaa aaatatttga   960
catagattga gcacctttt aacataattc caccataagt caattatgta gatgagaaat   1020
tggtacaaac aacgtggagc caaatcccac caaaccatct ctcatcctct cctataaaag  1080
gcttgctaca catagacaac aatccacaca aaaatacact taaaattctt ttcttctat   1140
ttggttaacc atgagtaaac ggaatccgaa gattctgaag atttttctgt atatgttact  1200
tctcaactct ctcttctca tcatctactt cgttttcac tcatcgtcgt tttcagagtc   1260
cagaatcagc aaccggttat cgagttccgc cacaaggacg gtacgagcct tcagaaatcg  1320
atgtcatgcc aggccaggga caccgggatc gagttacgga aatgcgaggc gaccgcttcc  1380
ctcggcacca gcgcctttac actacaatag cccaagtcgc gcagcgagtc attatccacg  1440
gtaccatgga ggttatgcgg acgacgtgac agttagcatg ggaccggacg acgatcgtac  1500
agatatcttt ggccccgaaa ccgatctcag cgaaacgcgc cacctcaacg acgcatacgg  1560
gtttcggtca tcccagatca ccctcagcga agatccccac ggcacccacg cgcgttcccg  1620
gtacgacgac gaagacgatg tgagcaccac ttattcctcc aacacgggca ccagcgcttc  1680
aggtgtcgac aagttcgagc attacggtcc cattccggag gaaggcaagc acgagcggcg  1740
cggcgtgcga ccaccacaga gtcgaggaa ggaagtccag ctcatcaacg gcgaactcgt   1800
tctcgagtgc aagattccga ctatattgta ttcgtttttg cccaggagag acgaagtgga  1860
gtttacgcac atgcggtaca cagccgtcac ttgtgaccct gatgactttg ttgccagggg  1920
ttacaagttg cgccagaata tcggtcgtac cgccagggag acgagctgt tcatctgcgt  1980
gaccatgtac aacgaggacg agttcggatt cacacggact atgcacgcag tgatgaagaa  2040
catttcgcat ttttgttccc gaaacaagag taggacgtgg ggagcggatg ggtggcagaa  2100
gattgtggtc tgtgtggttt cggatggacg agagatcatt cacccccgga ccttggacgc  2160
cctcgcagcc atgggcgttt accagcacgg tatcgccaag aactttgtca accagaaggc  2220
```

```
ggtgcaggcc cacgtttacg agtacacgac acaagtgtct ctggacagcg acctcaagtt    2280
caagggcgcc gagaagggca tcgtgccctg ccagatgatt ttttgcttga aggagaagaa    2340
ccaaaagaaa ctcaactcgc atagatggtt cttcaacgcc tttggcaaag ccttgaaccc    2400
gaatgtgtgt atcctcctag acgtcggcac ccgccccggc ggcacaagtc tctaccatct    2460
ctggaaagcc ttcgacacgg attccaacgt ggcggggcc tgcggggaaa tcaaagcgat    2520
gaaggggcgg tttggcggga atttgctcaa ccctctggtg gctagtcaga actttgagta    2580
caagatgagc aatattctgg acaaaccgtt ggagtcggtg tttgggtaca tcacggtgtt    2640
gccgggcgcc ttgtcggcgt atcggtacca tgcgctgcag aacgatgaga cgggccatgg    2700
gccgttgagt cagtatttca agggcgagac gctccatggg cagcacgcgg atgtgtttac    2760
ggcgaacatg tacttggccg aggaccgaat tctgtgttgg gagttggtgg ccaagagggg    2820
tgagaggtgg gtgttgaagt atgtgaaggg gtgtacgggt gagacggatg tgcctgacac    2880
cgtcccggaa ttcgtctcgc aacgtcgtcg ttggctcaac ggtgccttct tcgccgccgt    2940
ctactccctc gtccactttc gacaaatctg gaaaaccgac cacaccttta tgcgcaaagc    3000
ccttctccac gtcgaattcc tctaccacct cctgcaactc ctcttcacct acttctccct    3060
ggccaacttc tacctcgcct tctactttat cgccggcgga ctcgccgatc cccacgtcga    3120
cccttttaac tcggacggcc acgtcgcgcg catcatcttc aacatcctcc gctacgtctg    3180
cgtcctgctg atctgcacac aattcatctt gtccctcggc aaccgtccgc agggtgccaa    3240
aagaatgtat ctcgcatcca tgatcatcta cgccgtcatc atggtgtaca ccaccttcgc    3300
caccatcttc atcgtcgtgc gacaaatcca accctctcaa aaatccgacg acaagcccga    3360
cctcgaactc ggcaacaacg tcttcaccaa cctgatcgtc tccgtggcta gtaccctcgg    3420
gctctacttc gtcatgtcct ttctctatct cgaccctgg cacatgttca cctcggccat    3480
ccagtacttt gtcctgctgc cttcctacat ctgcacgctc cagatctacg ccttttgcaa    3540
cacccacgac gtcacatggg gcaccaaagg cgacaacgtg atgcgcaccg atctcggagg    3600
cgccattggc aagggaagca ccgtcgaact ggaaatgcct tcggaccaac tcgacatcga    3660
ctcgggatac gacgaatgtc tacgaaatct ccgggatcgc gtcatggtcc ctgccgttcc    3720
cgtgtccgag gaccagctgc agcaggatta ctacaagtcg gtgcgcacgt acatggtggt    3780
gtcgtggatg gtggccaacg cgacgctggc catggcggtg tcggaagcgt atggcgattc    3840
ggaaattggg gataattttt acttgcggtt tatcctgtgg gcggtggcgg ccctggcgct    3900
gtttagagcg ttggggtcga cgacgttttgc ggcgattaat ctggtgagtg ctctcgtgga    3960
gggcagggtc aggctgaggt tgaatatgaa agggtttagg tggattaagg agaagtgggg    4020
ggatgcggat gtgaagggca gtttgagggg gttgggggat cgggcgaggg ggttggcgag    4080
gcggtgagct agcaagcttg gacacgctga atcaccagt ctctctctac aaatctatct    4140 ctctctatt tctccataat aatgtgtgag tagttcccag ataagggaat tagggttcct    4200
atagggtttc gctcatgtgt tgagcatata agaaaccctt agtatgtatt tgtatttgta    4260
aaatacttct atcaataaaa tttctaattc ctaaaaccaa atccagtac taaaatccag    4320 atcatgcatg gtacagcacg cgtcctgcag gcccgggtta attaagcggc cgcaagctta    4380
aaatcactta tcaatttcaa aaacagaggt tagccgaatg ctaagagctt aaaaatggct    4440
tcttttgttt cttttttcttg caaacggtgg agagaagagg gaaatgaaga ttgaccatat    4500
ctttttttat tatgttttaa catataatat taataattta atcataatta tactttggtg    4560
```

```
aatgtgacag tggggatata cgtaaagtat ataacattat acttttttgca agcagttggc    4620 tggtctaccc aagagtgatc aaattttgag ctgccttcaa tgagccaatt tttgcctata    4680
atggataaag gcactttgtc tagttcaact gctcacagaa taatgttaaa atgaaattaa    4740
aacaaggtgg gctggtcaca ccaaaaaaat aaaatattaa tgtggtgttt ggttagtcga    4800
ttttatatta gttccatggc ataccgcctg gaaaggaaaa attcatgtaa ataatatatt    4860
tataaaaatt tatattaaaa ctaaatgaaa ttttagttga aatagttaag ttaaaaagag    4920
taaaatttat aatttatcat aattttatag aaattgagac taaaaaacat taagagaata    4980
aattctataa caaagacaat ttagtaaaaa tgtcctttta ggtaaatttta agtactctta    5040 accaaaataa aaaattcaaa tcaaattaac caaataagat aatataacat acggaacatc    5100
ccacttataa tcttcatacc ccgtaatctt attatgaaaa gtaatcttat attactcgaa    5160
tcaaatgctc tcacaaacta ttatctaaat aaagaaaaac acttaattttt tataacatttt   5220 tttttcatat atttgaaaga ttatattttg tattttttacg taaaaatatt tgacatagat    5280
tgagcacctt tttaacataa ttccaccata agtcaattat gtagatgaga aattggtaca    5340
aacaacgtgg agccaaatcc caccaaacca tctctcatcc tctcctataa aaggcttgct    5400
acacatagac aacaatccac acaaaaatac acttaaaatt cttttctttc tatttggtta    5460
accatgtgcg gaattgttgg tgctatcgcc caaagagacg ttgctgagat tttgttagag    5520
ggtctgcgaa ggctagagta tagaggatat gactccgctg gtctggctgt cgttgatgct    5580
gagggtcata tgacaaggct aagaaggtta ggaaaggttc agatgcttgc tcaggcagct    5640
gaggaacatc cattgcatgg aggtactggt attgcacata ccaggtgggc tactcatggg    5700
gagccatcag aagttaatgc tcatccacat gtgagtgagc atatcgttgt agttcacaat    5760
gggataattg aaaaccacga accattgagg gaagagttaa aggcaagagg atatactttt    5820
gtgagtgaga ctgacactga ggttattgca catttagtga actgggaact caaacagggg    5880
ggcacattgc gtgaggctgt gttaagagct attcctcaac ttagaggtgc atacggtact    5940
gttattatgg attcaagaca cccagatact ctccttgcag ctagatcagg tagtcccttg    6000
gtcataggac ttggaatggg tgaaaatttt atcgctagcg accaattggc cttattgcca    6060
gttacaagac gatttatttt ccttgaagag ggcgatattg ctgagattac tagaaggtct    6120
gtgaacatct ttgataagac tggcgctgag gttaaacgtc aggatatcga gtctaacctt    6180
caatacgatg ctggtgataa aggaatttac aggcattata tgcaaaagga aatttatgaa    6240
caaccaaatg ctatcaaaaa cacacttact ggccgtattt ctcatggaca ggtcgattta    6300
agcgagcttg gtcctaatgc agacgaactg ctatcaaaag ttgagcacat acagatactg    6360
gcatgcggaa ctagttataa ttcaggaatg gtgtctagat actggttcga aagcttggca    6420
ggtataccct tgtgatgtaga gatcgcttct gagtttaggt atagaaagtc tgctgtgcgt    6480
agaaattcat taatgattac attatctcaa tccggagaaa cagcagatac actggctgga    6540
ttgaggcttt ctaaggaact cggatatctg ggttcacttg ctatttgtaa tgtaccaggt    6600
tcctcattgg ttcgtgaatc agatctagca cttatgacaa atgcaggaac tgaaataggt    6660
gtggcaagta ccaaggcttt cacaacccaa ctgaccgtac ttttaatgtt ggtagcaaaa    6720
ctcagtcgat taaaggggct agatgcatct atcgaacatg atattgttca cgggcttcaa    6780
gctctccctt caagaattga acaaatgctt tcacaagata agagaataga ggcattggct    6840
gaagattttt ccgacaaaca tcgcgcattg tttcttggac gtggcgatca atatccaatt    6900
gcattggaag gagctttgaa gttgaaagaa ataagttaca ttcacgcaga agcatatgca    6960
```

```
gctggagaac tcaagcatgg tcctttggca ctcatcgacg ctgacatgcc cgtgatcgta    7020
gtggctccta ataacgaact gctcgaaaag cttaaatcaa atatcgaaga ggttcgagct    7080
agaggaggtc agctttacgt tttcgctgaa caagatgctg gattcgtgtc aagcgataat    7140
atgcatataa ttgaaatgcc tcacgttgaa gaagtgattg cacctatatt ttatacagtc    7200
ccattgcaac ttctagctta ccatgttgca cttattaaag gaactgatgt tgatcagcct    7260
agaaacctag caaaatctgt aacagtcgaa taaacgcgtg gcgcgccccc gatccgcgtt    7320
tgtgttttct gggtttctca cttaagcgtc tgcgttttac ttttgtattg ggtttggcgt    7380
ttagtagttt gcggtagcgt tcttgttatg tgtaattacg cttttttcttc ttgcttcagc    7440 agtttcggtt gaaatataaa tcgaatcaag tttcacttta tcagcgttgt tttaaatttt    7500
ggcattaaat tggtgaaaat tgcttcaatt ttgtatctaa atagaagaga caacatgaaa    7560
ttcgactttt gacctcaaat cttcgaacat ttatttcctg atttcacgat ggatgaggat    7620
aacgaagggg cggttcctat gtccgggaaa gttcccgtag aagacaatga gcaaagctac    7680
tgaaacgcgg acacgacgtc gcattggtac ggatatgagt taaaccgact caattccttt    7740
attaagacat aaaccgattt tggttaaagt gtaacagtga gctgatataa aaccgaaaca    7800
aaccggtaca agtttgattg agcaacttga tgacaaactt cagaattttg gttattgaat    7860
gaaaatcata gtctaatcgt aaaaaatgta cagaagaaaa gctagagcag aacaaagatt    7920
ctatattctg gttccaattt atcatcgctt taacgtccct cagatttgat cggggaattc    7980
gatatcatta ccctgttatc cctaaagctt attaatgttt gtcgaggaga atatgagtc    8040 gaggcatgga tacactaagt tcccctgaag tgagcatgat ctttgatgct gagatgattc    8100
ccagagcaag atagtttgtg ctgcaagtga cacaattgta atgaaaccac cactcaacga    8160
atttacttgt ggctttgaca tgtcgtgtgc tctgtttgta tttgtgagtg ccggttggta    8220 attattttttg ttaatgtgat tttaaaacct cttatgtaaa tagttacttt atctattgaa    8280
gtgtgttctt gtggtctata gtttctcaaa gggaaattaa aatgttgaca tcccatttac    8340
aattgataac ttggtataca caaactttgt aaatttggtg atatttatgg tcgaaagaag    8400
gcaataccca ttgtatgttc caatatcaat atcaatacga taacttgata atactaacat    8460
atgattgtca ttgttttttcc agtatcaata tacattaagc tactacaaaa ttagtataaa    8520
tcactatatt ataaatcttt ttcggttgta acttgtaatt cgtgggtttt taaaataaaa    8580
gcatgtgaaa attttcaaat aatgtgatgg cgcaattttta ttttccgagt tccaaaatat    8640
tgccgcttca ttaccctaat ttgtggcgcc acatgtaaaa caaaagacga ttcttagtgg    8700
ctatcactgc catcacgcgg atcactaata tgaaccgtcg attaaaacag atcgacggtt    8760
tatacatcat tttattgtac acacggatcg atatctcagc cgttagattt aatatgcgat    8820
ctgattgctc aaaaaataga ctctccgtct ttgcctataa aaacaatttc acatcttttct    8880 cacccaaatc tactccttaac cgttcttctt cttctacaga catcaatttc tctcgactct    8940
agaggatcca agcttatcga tttcgaaccc ctcaggcgaa gaacaggtat gatttgtttg    9000
taattagatc aggggtttag gtctttccat tacttttttaa tgttttttct gttactgtct    9060
ccgcgatctg attttacgac aatagagttt cgggttttgt cccattccag tttgaaaata    9120
aaggtccgtc ttttaagttt gctggatcga taaacctgtg aagattgagt ctagtcgatt    9180
tattggatga tccattcttc atcgttttttt tcttgcttcg aagttctgta taaccagatt    9240
tgtctgtgtg cgattgtcat tacctagccg tgtatcgaga actagggttt tcgagtcaat    9300
```

```
tttgcccctt ttggttatat ctggttcgat aacgattcat ctggattagg gttttaagtg    9360
gtgacgttta gtattccaat ttcttcaaaa tttagttatg gataatgaaa atccccaatt    9420
gactgttcaa tttcttgtta aatgcgcaga tcacaatggc ttcgatctcc tcctcagtcg    9480
cgaccgttag ccggaccgcc cctgctcagg ccaacatggg ggctccgttc accggcctta    9540
agtccaacgc cgccttcccc accaccaaga aggctaacga cttctccacc cttcccagca    9600
acggtggaag agttcaatgt atgcaggtgt ggccggccta cggcaacaag aagttcgaga    9660
cgctgtcgta cctgccgccg ctgtctatgg cgcccaccgt gatgatggcc tcgtcggcca    9720
ccgccgtcgc tccgttccag gggctcaagt ccaccgccag cctccccgtc gcccgccgct    9780
cctccagaag cctcggcaac gtcagcaacg gcggaaggat ccggtgcatg gccggcgccg    9840
aggagatcgt gctgcagccc atcaaggaga tctccggcac cgtcaagctg ccggggtcca    9900
agtcgctttc caaccggatc ctcctactcg ccgccctgtc cgagggaca acagtggttg    9960
ataacctgct gaacagtgag gatgtccact acatgctcgg ggccttgagg actcttggtc    10020
tctctgtcga agcggacaaa gctgccaaaa gagctgtagt tgttggctgt ggtggaaagt    10080
tcccagttga ggatgctaaa gaggaagtgc agctcttctt ggggaatgct ggaatcgcaa    10140
tgcggtcctt gacagcagct gttactgctg ctggtgaaa tgcaacttac gtgcttgatg    10200
gagtaccaag aatgagggag agacccattg gcgacttggt tgtcggattg aagcagcttg    10260
gtgcagatgt tgattgtttc cttggcactg actgcccacc tgttcgtgtc aatggaatcg    10320
gagggctacc tggtggcaag gtcaagctgt ctggctccat cagcagtcag tacttgagtg    10380
ccttgctgat ggctgctcct ttggctcttg gggatgtgga gattgaaatc attgataaat    10440
taatctccat tccgtacgtc gaaatgacat tgagattgat ggagcgtttt ggtgtgaaag    10500
cagagcattc tgatagctgg gacagattct acattaaggg aggtcaaaaa tacaagtccc    10560
ctaaaaatgc ctatgttgaa ggtgatgcct caagcgcaag ctatttcttg gctggtgctg    10620
caattactgg agggactgtg actgtggaag gttgtggcac caccagttg cagggtgatg    10680
tgaagtttgc tgaggtactg gagatgatgg gagcgaaggt tacatggacc gagactagcg    10740
taactgttac tggcccaccg cgggagccat ttgggaggaa acacctcaag gcgattgatg    10800
tcaacatgaa caagatgcct gatgtcgcca tgactcttgc tgtggttgcc ctctttgccg    10860
atggcccgac agccatcaga gacgtggctt cctggagagt aaaggagacc gagaggatgg    10920
ttgcgatccg gacggagcta accaagctgg gagcatctgt tgaggaaggg ccggactact    10980
gcatcatcac gccgccggag aagctgaacg tgacggcgat cgacacgtac gacgaccaca    11040
ggatggcgat ggcttttctcc cttgccgcct gtgccgaggt ccccgtcacc atccgggacc    11100
ctgggtgcac ccggaagacc ttccccgact acttcgatgt gctgagcact ttcgtcaaga    11160
attaagctct agaactagtg gatcccccga tccgcgtttg tgttttctgg gtttctcact    11220
taagcgtctg cgttttactt ttgtattggg tttggcgttt agtagtttgc ggtagcgttc    11280
ttgttatgtg taattacgct ttttcttctt gcttcagcag tttcggttga aatataaatc    11340
gaatcaagtt tcactttatc agcgttgttt taaattttgg cattaaattg gtgaaaattg    11400
cttcaatttt gtatctaaat agaagagaca acatgaaatt cgacttttga cctcaaatct    11460
tcgaacattt atttcctgat ttcacgatgg atgaggataa cgaaagggcg gttcctatgt    11520
ccgggaaagt tcccgtagaa gacaatgagc aaagctactg aaacgcggac acgacgtcgc    11580
attggtacgg atatgagtta aaccgactca attcctttat taagacataa accgattttg    11640
gttaaagtgt aacagtgagc tgatataaaa ccgaaacaaa ccggtacaag tttgattgag    11700
```

```
caacttgatg acaaacttca gaattttggt tattgaatga aaatcatagt ctaatcgtaa    11760
aaaatgtaca gaagaaaagc tagagcagaa caaagattct atattctggt tccaatttat    11820
catcgcttta acgtccctca gatttgatcg ggaaaccaaa acgtcgtgag acagtttggt    11880
taactataac ggtcctaagg tagcgatcga ggcattacgg cattacggca ctcgcgaggg    11940
tccgaattcg agcatggagc catttacaat tgaatatatc ctgccgccgc               11990
```